(12) United States Patent
Sakanishi et al.

(10) Patent No.: US 11,427,564 B2
(45) Date of Patent: Aug. 30, 2022

(54) HETEROARYL PYRIMIDINE COMPOUND AND PEST CONTROL AGENT

(71) Applicant: Nippon Soda Co., Ltd., Tokyo (JP)

(72) Inventors: Keita Sakanishi, Odawara (JP); Hikaru Aoyama, Odawara (JP); Norifumi Sakiyama, Odawara (JP); Takao Iwasa, Odawara (JP); Daisuke Ushijima, Odawara (JP); Maki Matsui, Odawara (JP)

(73) Assignee: Nippon Soda Co., Ltd., Tokyo (JP)

(*) Notice: Subject to any disclaimer, the term of this patent is extended or adjusted under 35 U.S.C. 154(b) by 304 days.

(21) Appl. No.: 16/624,636

(22) PCT Filed: Jun. 22, 2018

(86) PCT No.: PCT/JP2018/023819
§ 371 (c)(1),
(2) Date: Dec. 19, 2019

(87) PCT Pub. No.: WO2019/004082
PCT Pub. Date: Jan. 3, 2019

(65) Prior Publication Data
US 2020/0140414 A1 May 7, 2020

(30) Foreign Application Priority Data

Jun. 26, 2017 (JP) .............................. JP2017-124485
Apr. 24, 2018 (JP) .............................. JP2018-083512

(51) Int. Cl.
| | | |
|---|---|---|
| C07D 401/04 | (2006.01) | |
| C07D 401/14 | (2006.01) | |
| C07D 403/04 | (2006.01) | |
| C07D 403/14 | (2006.01) | |
| A01N 43/82 | (2006.01) | |

(52) U.S. Cl.
CPC .......... *C07D 401/14* (2013.01); *A01N 43/82* (2013.01); *C07D 401/04* (2013.01); *C07D 403/04* (2013.01); *C07D 403/14* (2013.01)

(58) Field of Classification Search
None
See application file for complete search history.

(56) References Cited

U.S. PATENT DOCUMENTS

| 7,238,697 | B2 | 7/2007 | Bretschneider et al. |
| 7,328,697 | B2 | 2/2008 | Turner et al. |
| 2003/0229125 | A1 | 12/2003 | Haaf et al. |
| 2004/0077641 | A1 | 4/2004 | Bretschneider et al. |
| 2018/0009778 | A1 | 1/2018 | Tanabe et al. |
| 2018/0297953 | A1 | 10/2018 | Tsuruda et al. |
| 2018/0297978 | A1 | 10/2018 | Orimoto et al. |
| 2018/0317485 | A1 | 11/2018 | Orimoto et al. |
| 2019/0040038 | A1 | 2/2019 | Tanabe et al. |

FOREIGN PATENT DOCUMENTS

| JP | 2004-524310 A | 8/2004 |
| JP | 2017-075161 A | 4/2017 |
| RU | 2304141 C2 | 6/2005 |
| RU | 2304141 C2 | 8/2007 |
| WO | WO 2010/064688 A1 | 6/2010 |
| WO | WO 2016/121969 A1 | 8/2016 |
| WO | WO 2017/065228 A1 | 4/2017 |
| WO | WO 2017/069105 A1 | 4/2017 |
| WO | WO 2017/073733 A1 | 5/2017 |
| WO | WO 2017/077911 A1 | 5/2017 |
| WO | WO 2017/150209 A1 | 9/2017 |
| WO | WO-2019/149260 A1 | 8/2019 |

OTHER PUBLICATIONS

Supplementary European Search Report dated Dec. 8, 2020 in EP 18823211.0.
International Search Report dated Jul. 24, 2018, in PCT/JP2018/023819.
Hauptman et al., Organic Chemistry, translated from German by P.B. Terentyev and S.S. Churanov, edited by V.M. Potapov, Moscow: Chemistry, 1979, 832 pages, p. 31, section 1.1.6.
Kaushik et al., "An assessment of structure and toxicity correlation in organochlorine pesticides," Journal of Hazardous Materials, 2007, 143:102-111.
Office Action dated Apr. 30, 2021, in RU 2019142439, with English translation, 18 pages.
Wikipedia entry for Ectoparasites, https://ru.wikipedia.org/wiki/Ectoparasites, 2 pages, last updated Apr. 27, 2021.

*Primary Examiner* — Alton N Pryor
(74) *Attorney, Agent, or Firm* — Foley & Lardner LLP

(57) ABSTRACT

A compound represented by a formula (I) or a salt thereof:

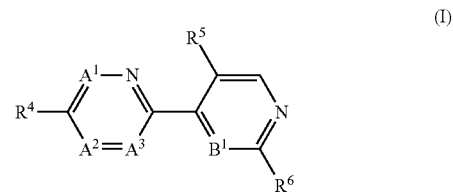

wherein $A^1$ represents $CR^1$ or a nitrogen atom; $A^2$ represents $CR^2$ or a nitrogen atom; $A^3$ represents $CR^3$ or a nitrogen atom, provided that two or more of $A^1$ to $A^3$ do not represent nitrogen atoms at the same time; $R^1$, $R^2$ and $R^3$ each independently represent a hydrogen atom or the like; $B^1$ represents CH or a nitrogen atom; $R^4$ represents a substituted or unsubstituted $C_{1-6}$ alkyl group or the like; $R^5$ represents a substituted or unsubstituted $C_{1-6}$ alkylthio group or the like; and $R^6$ represents a substituted or unsubstituted $C_{1-6}$ alkyl group or the like.

5 Claims, No Drawings

HETEROARYL PYRIMIDINE COMPOUND AND PEST CONTROL AGENT

TECHNICAL FIELD

The present invention relates to a heteroaryl pyrimidine compound and a pest control agent. More specifically, the present invention relates to a heteroaryl pyrimidine compound which has excellent insecticidal activity and/or acaricidal activity, is excellent in safety and can be synthesized in an industrially favorable manner, and a pest control agent containing this compound as an active ingredient.

Priority is claimed on Japanese Patent Application No. 2017-124485, filed Jun. 26, 2017, and Japanese Patent Application No. 2018-083512, filed Apr. 24, 2018, the contents of which are incorporated herein by reference.

BACKGROUND ART

Various compounds having insecticidal/acaricidal activities have been proposed. In order to put such a compound to practical use as an agricultural chemical, it is required not only to have sufficiently high efficacy, but also to be difficult to cause drug resistance, not to cause phytotoxicity to plants or soil pollution, and to have low toxicity to livestock and fish, or the like.

Incidentally, Patent Document 1 discloses a compound represented by a formula (A), and the like.

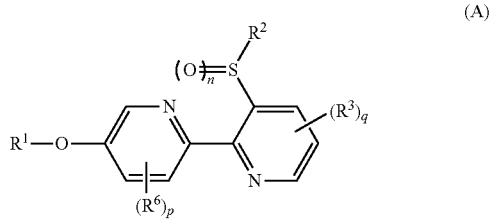
(A)

Patent Document 2 discloses a compound represented by a formula (B), and the like.

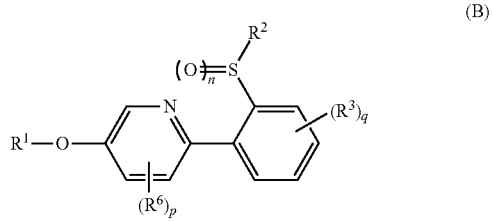
(B)

Patent Document 3 discloses a compound represented by a formula (C), and the like.

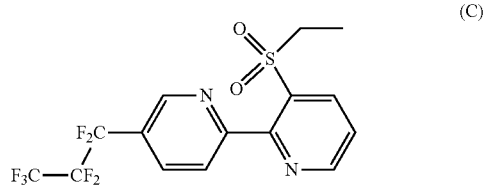 [SMILES: CCS(=O)(=O)c1cccnc1-c1ccc(C(F)(F)C(F)(F)C(F)(F)F)cn1]
(C)

CITATION LIST

Patent Documents

[Patent Document 1] WO2016/121969A
[Patent Document 2] WO2017/069105A
[Patent Document 3] WO2017/150209A

SUMMARY OF INVENTION

Technical Problem

An object of the present invention is to provide a heteroaryl pyrimidine compound which is excellent in pest control activity, in particular, insecticidal activity and/or acaricidal activity, excellent in safety and can be synthesized in an industrially favorable manner. Another object of the present invention is to provide a pest control agent, an insecticidal or acaricidal agent, an ectoparasite control agent, or an endoparasite control- or endoparasite-expelling agent containing a heteroaryl pyrimidine compound as an active ingredient.

Solution to Problem

As a result of intensive studies in order to solve the above problems, the present invention including the following embodiments has been completed.

[1] A compound represented by a formula (I) or a salt thereof.

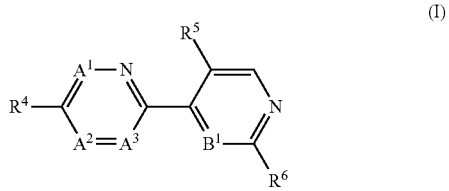
(I)

In the formula (I),
$A^1$ represents $CR^1$ or a nitrogen atom;
$A^2$ represents $CR^2$ or a nitrogen atom;
$A^3$ represents $CR^3$ or a nitrogen atom;
provided that two or more of $A^1$ to $A^3$ do not represent nitrogen atoms at the same time;
$R^1$, $R^2$ and $R^3$ each independently represent a hydrogen atom, a substituted or unsubstituted $C_{1-6}$ alkyl group, a hydroxyl group, a substituted or unsubstituted $C_{1-6}$ alkoxy group, a nitro group, a cyano group, a substituted or unsubstituted amino group or a halogeno group; $B^1$ represents CH or a nitrogen atom;
$R^4$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted C-6 alkoxy group, a formyl group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, a substituted or unsubstituted $C_{3-8}$ cycloalkyl group, a substituted or unsubstituted 5- to 6-membered heteroaryl group, a substituted or unsubstituted amino group, a substituted or unsubstituted aminocarbonyl group, or a group represented by —N=CR$^a$R$^b$, wherein R$^a$ represents a hydrogen atom or a C$_{1-6}$ alkyl group, and R$^b$ represents a C$_{1-6}$ alkyl group;

R$^5$ represents a substituted or unsubstituted C$_{1-6}$ alkylthio group, a substituted or unsubstituted C$_{1-6}$ alkylsulfinyl group, or a substituted or unsubstituted C$_{1-6}$ alkylsulfonyl group;

R$^6$ represents a substituted or unsubstituted C$_{1-6}$ alkyl group, a substituted or unsubstituted C$_{2-6}$ alkenyl group, a substituted or unsubstituted C$_{2-6}$ alkynyl group, a hydroxyl group, a substituted or unsubstituted C$_{1-6}$ alkoxy group, a substituted or unsubstituted C$_{1-6}$ alkoxycarbonyl group, a substituted or unsubstituted C$_{1-6}$ alkylthio group, a substituted or unsubstituted C$_{1-6}$ alkylsulfinyl group, a substituted or unsubstituted C$_{1-6}$ alkylsulfonyl group, a substituted or unsubstituted C$_{3-8}$ cycloalkyl group, a substituted or unsubstituted C$_{6-10}$ aryl group, a substituted or unsubstituted 5- to 6-membered heteroaryl group, a substituted or unsubstituted C$_{6-10}$ aryloxy group, a substituted or unsubstituted 5- to 6-membered heteroaryloxy group, a nitro group, a cyano group, a substituted or unsubstituted amino group, a substituted or unsubstituted aminocarbonyl group, a substituted or unsubstituted hydrazinyl group, a halogeno group, a group represented by —N—CHNR$^c$R$^d$, or —N=S(O)$_x$R$^e$R$^f$, wherein R$^c$, R$^d$, R$^e$ and R$^f$ are substituted or unsubstituted C$_{1-6}$ alkyl groups, and x is 0 or 1.

[2] A pest control agent containing at least one selected from the group consisting of the compound according to [1] above and a salt thereof as an active ingredient.

[3] An insecticidal or acaricidal agent containing at least one selected from the group consisting of the compound according to [1] above and a salt thereof as an active ingredient.

[4] An ectoparasite control agent containing at least one selected from the group consisting of the compound according to [1] above and a salt thereof as an active ingredient.

[5] An endoparasite control agent or endoparasite-expelling agent containing at least one selected from the group consisting of the compound according to [1] above and a salt thereof as an active ingredient.

Advantageous Effects of Invention

The heteroaryl pyrimidine compound of the present invention can control pests which are problematic in terms of agricultural crops and hygiene. In particular, agricultural pests and mites and ticks can be effectively controlled at lower concentrations. Furthermore, it is possible to effectively control ectoparasites and endoparasites which harm humans and animals.

DESCRIPTION OF EMBODIMENTS

[Heteroaryl Pyrimidine Compound]

The heteroaryl pyrimidine compound of the present invention is a compound represented by a formula (I) (hereinafter sometimes referred to as a compound (I)) or a salt of the compound (I).

(I)

In the present invention, the term "unsubstituted" means that it is composed only of a group which becomes a mother nucleus. When it is described only by the name of the group which becomes the mother nucleus without being described as "substituted", it means "unsubstituted" unless otherwise stated.

On the other hand, the term "substituted" means that any hydrogen atom of the group which is to become the mother nucleus is substituted with a group (substituent) having the same or different structure as that of the mother nucleus. Therefore, a "substituent" is another group bonded to a group which becomes a mother nucleus. The number of substituents may be one, or two or more. The two or more substituents may be the same or different.

The terms "C$_{1-6}$" and the like mean that the number of carbon atoms in the group which becomes a mother nucleus is 1 to 6, and so on. The number of carbon atoms does not include the number of carbon atoms present in the substituent. For example, a butyl group having an ethoxy group as a substituent is classified as a C2 alkoxy C4 alkyl group.

A "substituent" is not particularly limited as long as it is chemically acceptable and has the effects of the present invention. Hereinafter, groups which can be a "substituent" are exemplified.

A C$_{1-6}$ alkyl group such as a methyl group, an ethyl group, an n-propyl group, an i-propyl group, an n-butyl group, an s-butyl group, an i-butyl group, a t-butyl group, an n-pentyl group, and an n-hexyl group;

a C$_{2-6}$ alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a C$_{2-6}$ alkynyl group such as an ethynyl group, a 1-propynyl group, a 2-propynyl group, a 1-butynyl group, a 2-butynyl group, a 3-butynyl group, and a 1-methyl-2-propynyl group;

a C$_3$s cycloalkyl group such as a cyclopropyl group, a cyclobutyl group, a cyclopentyl group, a cyclohexyl group, and cubanyl group;

a C$_{6-10}$ aryl group such as a phenyl group and a naphthyl group;

a C$_{6-10}$ aryl C$_{1-6}$ alkyl group such as a benzyl group and a phenethyl group;

a 3- to 6-membered heterocyclyl group;

a 3- to 6-membered heterocyclyl C$_{1-6}$ alkyl group;

a hydroxyl group;

a C$_{1-6}$ alkoxy group such as a methoxy group, an ethoxy group, an n-propoxy group, an i-propoxy group, an n-butoxy group, an s-butoxy group, an i-butoxy group, and a t-butoxy group;

a C$_{2-6}$ alkenyloxy group such as a vinyloxy group, an allyloxy group, a propenyloxy group, and a butenyloxy group;

a C$_{2-6}$ alkynyloxy group such as an ethynyloxy group and a propargyloxy group; a C$_{6-10}$ aryloxy group such as a phenoxy group and a naphthoxy group;

a $C_{6-10}$ aryl $C_{1-6}$ alkoxy group such as a benzyloxy group and a phenethyloxy group;

a 5- to 6-membered heteroaryloxy group such as a thiazolyloxy group and a pyridyloxy group;

a 5- to 6-membered heteroaryl $C_{1-6}$ alkyloxy group such as a thiazolylmethyloxy group and a pyridylmethyloxy group;

a formyl group;

a $C_{1-6}$ alkylcarbonyl group such as an acetyl group and a propionyl group;

a formyloxy group;

a $C_{1-6}$ alkylcarbonyloxy group such as an acetyloxy group and a propionyloxy group;

a $C_{6-10}$ arylcarbonyl group such as a benzoyl group;

a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group;

a $C_{1-6}$ alkoxycarbonyloxy group such as a methoxycarbonyloxy group, an ethoxycarbonyloxy group, an n-propoxycarbonyloxy group, an i-propoxycarbonyloxy group, an n-butoxycarbonyloxy group and a t-butoxycarbonyloxy group;

a carboxyl group;

a halogeno groups such as a fluoro group, a chloro group, a bromo group, and an iodo group;

a $C_{1-6}$ haloalkyl group such as a chloromethyl group, a chloroethyl group, a difluoromethyl group, a trifluoromethyl group, a 2,2,2-trifluoroethyl group, a pentafluoroethyl group, a 1,2-dichloro-n-propyl group, a 1-fluoro-n-butyl group and a perfluoro-n-pentyl group;

a $C_{2-6}$ haloalkenyl group such as a 2-chloro-1-propenyl group and a 2-fluoro-1-butenyl group;

a $C_{2-6}$ haloalkynyl group such as a 4,4-dichloro-1-butynyl group, a 4-fluoro-1-pentynyl group, and a 5-bromo-2-pentynyl group;

a $C_{1-6}$ haloalkoxy group such as a trifluoromethoxy group, a 2-chloro-n-propoxy group, and a 2,3-dichlorobutoxy group;

a $C_{2-6}$ haloalkenyloxy group such as a 2-chloropropenyloxy group and a 3-bromobutenyloxy group;

a $C_{1-6}$ haloalkylcarbonyl group such as a chloroacetyl group, a trifluoroacetyl group and a trichloroacetyl group;

an amino group;

a $C_{1-6}$ alkyl-substituted amino group such as a methylamino group, a dimethylamino group and a diethylamino group;

a $C_{6-10}$ arylamino group such as an anilino group and a naphthylamino group;

a $C_{6-10}$ aryl $C_{1-6}$ alkylamino group such as a benzylamino group and a phenethylamino group;

a formylamino group;

a $C_{1-6}$ alkylcarbonylamino group such as an acetylamino group, a propanoylamino group, a butyrylamino group and an i-propylcarbonylamino group;

a $C_{1-6}$ alkoxycarbonylamino group such as a methoxycarbonylamino group, an ethoxycarbonylamino group, an n-propoxycarbonylamino group and an i-propoxycarbonylamino group;

an unsubstituted or substituted aminocarbonyl group such as an aminocarbonyl group, a dimethylaminocarbonyl group, a phenylaminocarbonyl group and an N-phenyl-N-methylaminocarbonyl group;

an imino $C_{1-6}$ alkyl group such as an iminomethyl group, a (1-imino)ethyl group and a (1-imino)-n-propyl group;

a substituted or unsubstituted N-hydroxyimino $C_{1-6}$ alkyl group such as an N-hydroxy-iminomethyl group, a (1-(N-hydroxy)-imino)ethyl group, a (1-(N-hydroxy)-imino)propyl group, an N-methoxy-iminomethyl group, and a (1-(N-methoxy)-imino)ethyl group;

an aminocarbonyloxy group;

a $C_{1-6}$ alkyl-substituted aminocarbonyloxy group such as an ethylaminocarbonyloxy group, and a dimethylaminocarbonyloxy group;

a mercapto group;

a $C_{1-6}$ alkylthio group such as a methylthio group, an ethylthio group, an n-propylthio group, an i-propylthio group, an n-butylthio group, an i-butylthio group, an s-butylthio group and a t-butylthio group;

a $C_{1-6}$ haloalkylthio group such as a trifluoromethylthio group and a 2,2,2-trifluoroethylthio group;

a $C_{6-10}$ arylthio group such as a phenylthio group and a naphthylthio group; a 5- to 6-membered heteroarylthio group such as a thiazolylthio group and a pyridylthio group;

a $C_{1-6}$ alkylsulfinyl group such as a methylsulfinyl group, an ethylsulfinyl group and a t-butylsulfinyl group;

a $C_{1-6}$ haloalkylsulfinyl group such as a trifluoromethylsulfinyl group and a 2,2,2-trifluoroethylsulfinyl group;

a $C_{6-10}$ arylsulfinyl group such as a phenylsulfinyl group;

a 5- to 6-membered heteroarylsulfinyl group such as a thiazolylsulfinyl group and a pyridylsulfinyl group;

a $C_{1-6}$ alkylsulfonyl group such as a methylsulfonyl group, an ethylsulfonyl group and a t-butylsulfonyl group;

a $C_{1-6}$ haloalkylsulfonyl group such as a trifluoromethylsulfonyl group and a 2,2,2-trifluoroethylsulfonyl group;

a $C_{6-10}$ arylsulfonyl group such as a phenylsulfonyl group;

a 5- to 6-membered heteroarylsulfonyl group such as a thiazolylsulfonyl group and a pyridylsulfonyl group;

a $C_{1-6}$ alkylsulfonyloxy group such as a methylsulfonyloxy group, an ethylsulfonyloxy group and a t-butylsulfonyloxy group;

a $C_{1-6}$ haloalkylsulfonyloxy group such as a trifluoromethylsulfonyloxy group and a 2,2,2-trifluoroethylsulfonyloxy group;

a tri $C_{1-6}$ alkyl-substituted silyl group such as a trimethylsilyl group, a triethylsilyl group and a t-butyldimethylsilyl group;

a tri $C_{6-10}$ aryl-substituted silyl group such as a triphenylsilyl group;

a cyano group; a nitro group.

Further, in these "substituents", any hydrogen atom in the substituent may be substituted with a group having a different structure. Examples of the "substituent" in this case include a $C_{1-6}$ alkyl group, a $C_{1-6}$ haloalkyl group, a $C_{1-6}$ alkoxy group, a $C_{1-6}$ haloalkoxy group, a halogeno group, a cyano group and a nitro group.

Further, the above-described "3- to 6-membered heterocyclyl group" includes 1 to 4 hetero atoms selected from the group consisting of a nitrogen atom, an oxygen atom and a sulfur atom as constituent atoms of the ring. The heterocyclyl group may be either monocyclic or polycyclic. As long as the polycyclic heterocyclyl group includes at least one heterocyclic ring, the remaining ring may be any of a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, and a 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group.

Examples of the 6-membered heteroaryl group include a pyridyl group, a pyrazinyl group, a pyrimidinyl group, a pyridazinyl group and a triazinyl group.

[$A^1$, $A^2$, $A^3$]

In the formula (I), $A^1$ represents $CR^1$ or a nitrogen atom, $A^2$ represents $CR^2$ or a nitrogen atom, and $A^3$ represents $CR^3$ or a nitrogen atom. However, two or more of $A^1$ to $A^3$ do not represent nitrogen atoms at the same time.

That is, the compound represented by the formula (I) is a compound represented by formulas (II) to formula (V).

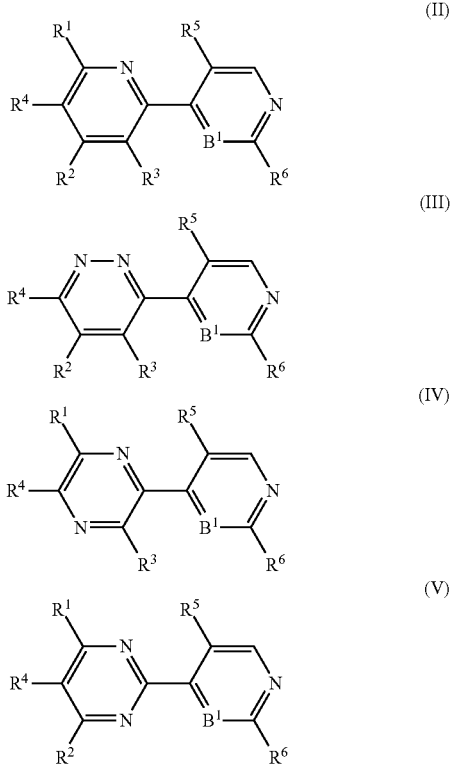

In the formulas (II) to (V), $B^1$, $R^4$, R and $R^6$ are the same as those defined in the formula (I). The compound represented by the formula (I) is preferably a compound represented by the formula (II) or formula (III).

$R^1$, $R^2$ and $R^3$ each independently represent a hydrogen atom, a substituted or unsubstituted $C_{1-6}$ alkyl group, a hydroxyl group, a substituted or unsubstituted $C_{1-6}$ alkoxy group, a nitro group, a cyano group, a substituted or unsubstituted amino group or a halogeno group.

The "$C_{1-6}$ alkyl group" represented by $R^1$, $R^2$ and $R^3$ may be linear, or may be branched as long as it has 3 or more carbon atoms. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Examples of the "$C_{1-6}$ alkoxy group" represented by $R^1$, $R^2$ and $R^3$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group and an i-hexyloxy group.

Preferred examples of the substituent on the "$C_{1-6}$ alkyl group" and "$C_{1-6}$ alkoxy group" represented by $R^1$, $R^2$ and $R^3$ include a $C_{1-6}$ alkoxy group such as a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group and an i-hexyloxy group; a halogeno group such as a fluoro group, a chloro group, a bromo group and an iodo group; a cyano group; a $C_{3-8}$ cycloalkyl group such as a cyclopropyl group, a cyclobutyl group, a cyclopentyl group, a cyclohexyl group and a cubanyl group; a $C_{6-10}$ aryl group such as a phenyl group and a naphthyl group; and a 5- to 6-membered heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, a pyridyl group, a pyrazinyl group, a pyrimidinyl group, a pyridazinyl group and a triazinyl group.

The "substituted or unsubstituted amino group" represented by $R^1$, $R^2$ and $R^3$ is a group represented by "—$NR^gR^h$". In the formula, $R^g$ and $R^h$ each independently represents a hydrogen atom, a $C_{1-6}$ alkyl group, a formyl group, a $C_{1-6}$ alkylcarbonyl group, a $C_{1-6}$ haloalkylcarbonyl group, a $C_{3-8}$ cycloalkylcarbonyl group, a $C_{1-6}$ alkoxycarbonyl group, a substituted or unsubstituted amidino group, a substituted or unsubstituted aminocarbonyl group, a substituted or unsubstituted aminosulfonyl group, or a $C_{1-6}$ haloalkylsulfonyl group.

Examples of the "$C_{1-6}$ alkyl group" represented by $R^g$ and $R^h$ include the same groups as those exemplified above for $R^1$, $R^2$ and $R^3$.

Examples of the "$C_{1-6}$ alkylcarbonyl group" represented by $R^g$ and $R^h$ include an acetyl group, a propionyl group and an isobutyryl group.

Examples of the "$C_{1-6}$ haloalkylcarbonyl group" represented by $R^g$ and $R^h$ include a trifluoroacetyl group.

Examples of the "$C_{3-8}$ cycloalkylcarbonyl group" represented by $R^g$ and $R^h$ include a cyclopropylcarbonyl group, a cyclobutylcarbonyl group, a cyclopentylcarbonyl group and a cyclohexylcarbonyl group.

Examples of the "$C_{1-6}$ alkoxycarbonyl group" represented by $R^g$ and $R^h$ include a methoxycarbonyl group, an ethoxycarbonyl group, an n-propoxycarbonyl group, an i-propoxycarbonyl group, an n-butoxycarbonyl group and a t-butoxycarbonyl group.

Preferred examples of the substituent on the "amidino group" represented by $R^g$ and $R^h$ include a $C_{1-6}$ alkyl group such as a methyl group, an ethyl group, an n-propyl group, an i-propyl group, an n-butyl group, an s-butyl group, an i-butyl group, a t-butyl group, an n-pentyl group, and an n-hexyl group; a formyl group; a $C_{1-6}$ alkylcarbonyl group such as an acetyl group and a propionyl group; and a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group.

Examples of the "substituted or unsubstituted aminocarbonyl group" represented by $R^g$ and $R^h$ include an aminocarbonyl group, a methylaminocarbonyl group, an ethylaminocarbonyl group, and a dimethylaminocarbonyl group.

Examples of the "substituted or unsubstituted aminosulfonyl group" represented by $R^g$ and $R^h$ include an aminosulfonyl group, a methylaminosulfonyl group, and a dimethylaminosulfonyl group.

$R^g$ is preferably a hydrogen atom, a $C_{1-6}$ alkyl group, a $C_{1-6}$ alkylcarbonyl group, a $C_{3-8}$ cycloalkylcarbonyl group, or a substituted or unsubstituted aminocarbonyl group.

Examples of the "$C_{1-6}$ haloalkylsulfonyl group" represented by $R^g$ and $R^h$ include a trifluoromethylsulfonyl group.

$R^h$ is preferably a hydrogen atom or a $C_{1-6}$ alkyl group.

Examples of the "halogeno group" represented by $R^1$, $R^2$ and $R^3$ include a fluoro group, a chloro group, a bromo group, and an iodo group.

$R^1$, $R^2$ and $R^3$ are preferably hydrogen atoms.

[$B^1$]

In the formula (I), $B^1$ represents CH or a nitrogen atom.

That is, the compound represented by the formula (I) is a compound represented by the formula (VI) to the formula (VII).

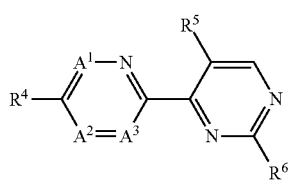

(VI)

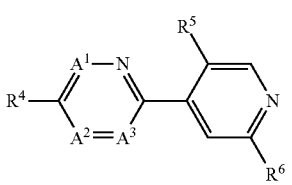

(VII)

In the formulas (VI) to (VII), $A^1$, $A^2$, $A^3$, $R^4$, $R^5$ and $R^6$ are the same as those defined in the formula (I).

$B^1$ is preferably a nitrogen atom.

[$R^4$]

In the formula (I), $R^4$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a formyl group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, a substituted or unsubstituted $C_{3-8}$ cycloalkyl group, a substituted or unsubstituted 5- to 6-membered heteroaryl group, a substituted or unsubstituted amino group, a substituted or unsubstituted aminocarbonyl group, or a group represented by $-N=CR^aR^b$. Here, $R^a$ represents a hydrogen atom or a $C_{1-6}$ alkyl group, and $R^b$ represents a $C_{1-6}$ alkyl group.

Examples of the "$C_{1-6}$ alkyl group", "$C_{1-6}$ alkoxy group", and "substituted or unsubstituted amino group" represented by $R^4$ include the same groups as those exemplified above for $R^1$, $R^2$ and $R^3$.

Examples of the "$C_{1-6}$ alkylcarbonyl group" and "$C_{1-6}$ alkoxycarbonyl group" represented by $R^4$ include the same groups as those exemplified above for $R^g$ and $R^h$.

Specific examples of the "substituted $C_{1-6}$ alkyl group" represented by $R^4$ include a $C_{1-6}$ haloalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; and a $C_{1-6}$ haloalkoxyimino $C_{1-6}$ alkyl group such as a 2,2,3,3,3-pentafluoropropoxyiminomethyl group and a 2,2,3,3,4,4,4-heptafluorobutoxyiminomethyl group.

Specific examples of the "substituted $C_{1-6}$ alkoxy group" represented by $R^4$ include a $C_{1-6}$ haloalkoxy group such as a chloromethoxy group, a dichloromethoxy group, a difluoromethoxy group, a trichloromethoxy group, a trifluoromethoxy group, a 1-fluoroethoxy group, a 1,1-difluoroethoxy group, a 2,2,2-trichloroethoxy group, a 2,2,2-trifluoroethoxy group, a pentafluoroethoxy group, a 2,2,3,3-tetrafluoropropoxy group, a 2,2,3,3,3-pentafluoropropoxy group, a 2,2,3,4,4,4-hexafluorobutoxy group, a 2,2,3,3,4,4,4-heptafluorobutoxy group and a 2,2,3,3,4,4,5,5-octafluoropentyloxy group; a $C_{6-10}$ aryl $C_{1-6}$ alkoxy group such as a benzyloxy group and a phenethyloxy group; and a $C_{3-8}$ cycloalkyl $C_{1-6}$ alkoxy group such as a cyclopropylmethyloxy group.

Examples of the "$C_{2-6}$ alkenyl group" represented by $R^4$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "$C_{2-6}$ alkynyl group" represented by $R^4$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group.

Specific examples of the "substituted $C_{2-6}$ alkynyl group" include a $C_{2-6}$ haloalkynyl group such as a 4,4-dichloro-1-butynyl group, a 4-fluoro-1-pentynyl group, and a 5-bromo-2-pentynyl group.

Examples of the "$C_{1-6}$ alkylthio group" represented by $R^4$ include a methylthio group, an ethylthio group, an n-propylthio group, an n-butylthio group, an n-pentylthio group, an n-hexylthio group, an i-propylthio group and an i-butylthio group.

Examples of the "$C_{1-6}$ alkylsulfinyl group" represented by $R^4$ include a methylsulfinyl group, an ethylsulfinyl group and a t-butylsulfinyl group.

Examples of the "$C_{1-6}$ alkylsulfonyl group" represented by $R^4$ include a methylsulfonyl group, an ethylsulfonyl group and a t-butylsulfonyl group.

Examples of the "$C_{1-6}$ alkylsulfonyloxy group" represented by $R^4$ include a methylsulfonyloxy group and an ethylsulfonyloxy group.

Preferred examples of the substituent on the "$C_{1-6}$ alkyl group", "$C_{2-6}$ alkenyl group", "$C_{2-6}$ alkynyl group", "$C_{1-6}$ alkoxy group", "$C_{1-6}$ alkylcarbonyl group", "$C_{1-6}$ alkoxycarbonyl group", "$C_{1-6}$ alkylthio group", "$C_{1-6}$ alkylsulfinyl group", "$C_{1-6}$ alkylsulfonyl group", and "$C_{1-6}$ alkylsulfonyloxy group" represented by $R^4$ include a halogeno group such as a fluoro group, a chloro group, a bromo group and an iodo group; a $C_{3-8}$ cycloalkyl group such as a cyclopropyl group, a cyclobutyl group, a cyclopentyl group, a cyclohexyl group and a cubanyl group; a phenyl group; and a $C_{1-6}$ haloalkoxyimino group such as a 2,2,3,3,3-pentafluoropropoxyimino group and a 2,2,3,3,4,4,4-heptafluorobutoxyimino group; and a halogeno group such as a fluoro group, a chloro group, a bromo group and an iodo group is more preferred.

Examples of the "$C_{3-8}$ cycloalkyl group" represented by $R^4$ include a cyclopropyl group, a cyclobutyl group, a cyclopentyl group, a cyclohexyl group, and a cubanyl group.

Examples of the "5- to 6-membered heteroaryl group" represented by $R^4$ include 5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group (more specifically, a [1,2,3]triazolyl group or a [1,2,4] triazolyl group), an oxadiazolyl group (more specifically, a [1,2,4] oxadiazolyl group or a [1,3,4] oxadiazolyl group), a thiadiazolyl group and a tetrazolyl group; and 6-membered heteroaryl groups such as a pyridyl group, a pyrazinyl group, a pyrimidinyl group, a pyridazinyl group, and a triazinyl group.

Preferred examples of the substituent on the "$C_{3-8}$ cycloalkyl group" and the "5- to 6-membered heteroaryl group" represented by $R^4$ include a halogeno group such as a fluoro group, a chloro group, a bromo group and an iodo group; a $C_{1-6}$ haloalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; and a $C_{2-6}$ alkenyl group such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "substituted or unsubstituted aminocarbonyl group" represented by $R^4$ include the same groups as those exemplified above for $R^g$ and $R^h$.

Examples of the "$C_{1-6}$ alkyl group" represented by $R^e$ and $R^b$ in the group represented by "—N=$CR^aR^b$" include the same groups as those exemplified above for $R^1$, $R^2$ and $R^3$.

$R^4$ is preferably a substituted or unsubstituted $C_{1-6}$ alkyl group, or a substituted or unsubstituted $C_{1-6}$ alkoxy group, and more preferably a $C_{1-6}$ haloalkyl group, a $C_{1-6}$ alkoxy group, or a $C_{1-6}$ haloalkoxy group.

[$R^5$]

In the formula (I), $R^5$ is a substituted or unsubstituted $C_{1-6}$ alkylthio group, a substituted or unsubstituted $C_{1-6}$ alkylsulfinyl group, or a substituted or unsubstituted $C_{1-6}$ alkylsulfonyl group.

Examples of the "substituted or unsubstituted $C_{1-6}$ alkylthio group", "substituted or unsubstituted $C_{1-6}$ alkylsulfinyl group" and "substituted or unsubstituted $C_{1-6}$ alkylsulfonyl group" represented by $R^5$ include the same groups as those exemplified above for $R^4$.

$R^5$ is preferably a $C_{1-6}$ alkylsulfinyl group or a $C_{1-6}$ alkylsulfonyl group, and particularly preferably a $C_{1-6}$ alkylsulfonyl group.

[$R^6$]

In the formula (I), $R^6$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{3-8}$ cycloalkyl group, a substituted or unsubstituted $C_{6-10}$ aryl group, a substituted or unsubstituted 5- to 6-membered heteroaryl group, a substituted or unsubstituted $C_{6-10}$ aryloxy group, a substituted or unsubstituted 5- to 6-membered heteroaryloxy group, a nitro group, a cyano group, a substituted or unsubstituted amino group, a substituted or unsubstituted aminocarbonyl group, a substituted or unsubstituted hydrazinyl group, a halogeno group, a group represented by —N—CHNR$^c$R$^d$, or —N=$S(O)_xR^eR^f$. Here, $R^c$, $R^d$, $R^e$ and $R^f$ are substituted or unsubstituted $C_{1-6}$ alkyl groups, and x is 0 or 1.

Examples of the "$C_{1-6}$ alkyl group", "$C_{1-6}$ alkoxy group", "substituted or unsubstituted amino group" and "halogeno group" represented by $R^6$ include the same groups as those exemplified above for $R^1$, $R^2$ and $R^3$.

Examples of the "$C_{1-6}$ alkoxycarbonyl group" and "substituted or unsubstituted aminocarbonyl group" represented by $R^6$ include the same groups as those exemplified above for $R^g$ and $R^h$.

Examples of the "$C_{2-6}$ alkenyl group", "$C_{2-6}$ alkynyl group", "$C_{1-6}$ alkylthio group", "$C_{1-6}$ alkylsulfinyl group", "$C_{1-6}$ alkylsulfonyl group", "$C_{3-8}$ cycloalkyl group" and "5- to 6-membered heteroaryl group" represented by $R^6$ include the same groups as those exemplified above for $R^4$.

Preferred examples of the substituent on the "$C_{1-6}$ alkyl group", "$C_{2-6}$ alkenyl group", "$C_{2-6}$ alkynyl group", "$C_{1-6}$ alkoxycarbonyl group", "$C_{1-6}$ alkylthio group", "$C_{1-6}$ alkylsulfinyl group" and "$C_{1-6}$ alkylsulfonyl group" represented by $R^6$ include a halogeno group such as a fluoro group, a chloro group, a bromo group and an iodo group; and a $C_{3-8}$ cycloalkyl group such as a cyclopropyl group, a cyclobutyl group, a cyclopentyl group, a cyclohexyl group and a cubanyl group.

Examples of the "$C_{6-10}$ aryl group" represented by $R^6$ include a phenyl group and a naphthyl group.

Examples of the "$C_{6-10}$ aryloxy group" represented by $R^6$ include a phenoxy group, a naphthyloxy group, an azulenyloxy group, an indenyloxy group, an indanyloxy group, and a tetralinyloxy group.

Examples of the "5- to 6-membered heteroaryloxy group" represented by $R^6$ include a thiazolyloxy group and a pyridyloxy group.

Preferred examples of the substituent on the "$C_{3-8}$ cycloalkyl group", "$C_{6-10}$ aryl group", "heteroaryl group", "$C_{6-10}$ aryloxy group", and "5- to 6-membered heteroaryloxy group" represented by $R^6$ include a halogeno group such as a fluoro group, a chloro group, a bromo group and an iodo group; a $C_{1-6}$ alkyl group such as a methyl group, an ethyl group, an n-propyl group, an i-propyl group, an n-butyl group, an s-butyl group, an i-butyl group, a t-butyl group, an n-pentyl group and an n-hexyl group; a $C_{1-6}$ haloalkyl group such as a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a perfluoropropyl group, a 2,2,2-trifluoro-1-trifluoromethylethyl group, a perfluoroisopropyl group, a 4-fluorobutyl group, a 2,2,3,3,4,4,4-heptafluorobutyl group, a perfluorobutyl group, a perfluoropentyl group, a perfluorohexyl group, a chloromethyl group, a bromomethyl group, a dichloromethyl group, a dibromomethyl group, a trichloromethyl group, a tribromomethyl group, a 1-chloroethyl group, a 2,2,2-trichloroethyl group, a 4-chlorobutyl group, a perchlorohexyl group and a 2,4,6-trichlorohexyl group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; a $C_{3-8}$ cycloalkyl $C_{1-6}$ alkyl group such as a cyclopropylmethyl group; a $C_{1-6}$ alkylcarbonyl group such as an acetyl group and a propionyl group; an amino group; a cyano group; and a (2-(trimethylsilyl) ethoxy) methyl group can be exemplified, and more preferred examples of the substituent include a halogeno group, a $C_{1-6}$ alkyl group, a $C_{1-6}$ haloalkyl group and an amino group.

The "substituted or unsubstituted hydrazinyl group" represented by $R^6$ is a group represented by the formula (f).

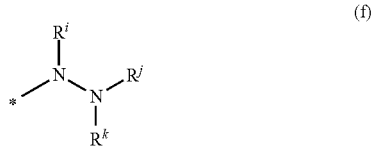

(f)

In the formula (f), the symbol * represents a bonding position, and $R^i$, $R^j$, and $R^k$ each independently represent a hydrogen atom, a $C_{1-6}$ alkyl group, or a substituted or unsubstituted phenylsulfonyl group.

Examples of the "$C_{1-6}$ alkyl group" represented by $R^i$, $R^j$, and $R^k$ include the same groups as those exemplified above for $R^1$, $R^2$ and $R^3$.

Examples of the "substituted phenylsulfonyl group" represented by $R^i$, $R^j$, and $R^k$ include a paratoluenesulfonyl group.

$R^i$ is preferably a hydrogen atom or a $C_{1-6}$ alkyl group.
$R^j$ and $R^k$ are preferably hydrogen atoms.

Examples of the "$C_{1-6}$ alkyl group" represented by $R^c$ and $R^d$ in the group represented by "—N—CHNR$^c$R$^d$" include the same groups as those exemplified above for $R^1$, $R^2$ and $R^3$.

Examples of the "$C_{1-6}$ alkyl group" represented by $R^e$ and $R^f$ in the group represented by "—N=S(O)$_x$R$^e$R$^f$" include the same groups as those exemplified above for $R^1$, $R^2$ and $R^3$.

$R^6$ is preferably a substituted or unsubstituted $C_{1-6}$ alkyl group, a substituted or unsubstituted $C_{1-6}$ alkoxy group, a substituted or unsubstituted $C_{6-10}$ aryl group, a substituted or unsubstituted 5- to 6-membered heteroaryl group, a cyano group, a substituted or unsubstituted amino group, or a substituted or unsubstituted hydrazinyl group, and more preferably a $C_{1-6}$ alkyl group, a $C_{1-6}$ alkoxy group, a substituted or unsubstituted phenyl group, a substituted or unsubstituted 5- to 6-membered heteroaryl group, a cyano group, a substituted or unsubstituted amino group, or a substituted or unsubstituted hydrazinyl group.

The salt of compound (I) is not particularly limited as long as it is an agriculturally and horticulturally acceptable salt. Examples of the salt of compound (I) include salts of inorganic acids such as hydrochloric acid and sulfuric acid; salts of organic acids such as acetic acid and lactic acid; salts of alkali metals such as lithium, sodium and potassium; salts of alkaline earth metals such as calcium and magnesium; salts of transition metals such as iron and copper; and salts of organic bases such as ammonia, triethylamine, tributylamine, pyridine and hydrazine.

The compound (I) or the salt of the compound (I) is not particularly limited by the production method thereof. For example, the compound (I) or the salt of the compound (I) of the present invention can be obtained by a known production method described in Examples and the like. Further, the salt of the compound (I) can be obtained from the compound (I) by a known method.

The compound represented by the formula (I) is preferably a compound represented by the formula (VI).

In the formula (VI), $A^2$ is preferably $CR^2$, $A^3$ is preferably $CR^3$, $R^4$ is preferably a substituted or unsubstituted $C_{1-6}$ alkyl group, or a substituted or unsubstituted $C_{1-6}$ alkoxy group, $R^5$ is preferably an alkylsulfonyl group, and $R^6$ is preferably a $C_{1-6}$ alkyl group, a $C_{1-6}$ alkoxy group, a substituted or unsubstituted phenyl group, a substituted or unsubstituted 5- to 6-membered heteroaryl group, a cyano group, a substituted or unsubstituted amino group, or a substituted or unsubstituted hydrazinyl group.

The compound represented by the formula (I) is preferably a compound represented by the formula (VII).

In the formula (VII), $A^1$ is preferably $CR^1$, $A^2$ is preferably $CR^2$, $A^3$ is preferably $CR^3$, $R^4$ is preferably a substituted or unsubstituted $C_{1-6}$ alkoxy group, $R^5$ is preferably an alkylsulfonyl group, and $R^6$ is preferably a $C_{1-6}$ alkoxy group.

The heteroaryl pyrimidine compound of the present invention is excellent in the effect of controlling harmful organisms such as various agricultural pests and mites and ticks which adversely affect the growth of plants.

Further, the heteroaryl pyrimidine compound of the present invention is a highly safe substance because it has little phytotoxicity to crops and has low toxicity to fish and warm-blooded animals. Therefore, it is useful as an active ingredient of an insecticide or acaricide.

Furthermore, in recent years, resistance to various existing drugs has developed in a number of insect pests such as diamondback moths, planthoppers, leafhoppers and aphids, causing problems of insufficient efficacy of these drugs, and drugs that are effective even against the resistant strains of insect pests have been desired. The heteroaryl pyrimidine compound of the present invention exhibits an excellent control effect not only on susceptible strains but also on various resistant strains of insect pests and acaricide-resistant strains of mites and ticks.

The heteroaryl pyrimidine compound of the present invention is excellent in the effect of controlling ectoparasites and endoparasites which are harmful to humans and animals. In addition, it is a highly safe substance because of its low toxicity to fish and warm-blooded animals. Therefore, it is useful as an active ingredient of an agent for controlling ectoparasites and endoparasites.

In addition, the heteroaryl pyrimidine compound of the present invention shows efficacy in all developmental stages of organisms to be controlled, and shows excellent control effects, for example, on eggs, nymphs, larvae, pupae and adults of mites and ticks, insects and the like.

[Pest Control Agent]

The pest control agent of the present invention contains at least one selected from the heteroaryl pyrimidine compounds of the present invention as an active ingredient. The amount of the heteroaryl pyrimidine compound contained in the pest control agent of the present invention is not particularly limited as long as the pest control effects are exhibited. The pest control agent is an agent for controlling pests, and includes an insecticidal or acaricidal agent, an ectoparasite control agent, or an endoparasite control- or endoparasite-expelling agent, and the like.

[Insecticidal or Acaricidal Agent]

The insecticidal or acaricidal agent of the present invention contains at least one selected from the heteroaryl pyrimidine compounds of the present invention as an active ingredient. The amount of the heteroaryl pyrimidine compound contained in the insecticidal or acaricidal agent of the present invention is not particularly limited as long as it exhibits an insecticidal or acaricidal effect.

The pest control agent or the insecticidal or acaricidal agent of the present invention is preferably used for grains; vegetables; root vegetables; potatoes; flowers and ornamental plants; fruit trees; foliage plants and trees of tea, coffee, cacao and the like; pasture grasses; turf grasses; and plants such as cotton.

In application to plants, the pest control agent or the insecticidal or acaricidal agent of the present invention may be used to any portions of leaves, stems, stalks, flowers, buds, fruits, seeds, sprouts, roots, tubers, tuberous roots, shoots, cuttings and the like.

Further, the pest control agent or the insecticidal or acaricidal agent of the present invention is not particularly limited by the species of the plant to be applied. Examples of the plant species include an original species, a variant species, an improved variety, a cultivar, a mutant, a hybrid and a genetically modified organism (GMO).

The pest control agent of the present invention can be used for seed treatment, foliage application, soil application, water surface application and the like, in order to control various agricultural pests and mites and ticks.

Specific examples of various agricultural pests and mites and ticks which can be controlled by the pest control agent of the present invention are shown below.

(1) Butterflies or Moths of the Order Lepidoptera
  (a) Moths of the family Arctiidae such as *Hyphantria cunea* and *Lemyra imparilis*;
  (b) moths of the family Bucculatricidae such as *Bucculatrix pyrivorella*;
  (c) moths of the family Carposinidae such as *Carposina sasakii*;
  (d) moths of the family Crambidae, for example, species belonging to the genus *Diaphania* (*Diaphania* spp.) such as *Diaphania indica* and *Diaphania nitidalis*; for example, species belonging to the genus *Ostrinia* (*Ostrinia* spp.) such as *Ostrinia furnacalis*, *Ostrinia nubilalis* and *Ostrinia scapulalis*; and others such as *Chilo suppressalis*, *Cnaphalocrocis medinalis*, *Conogethes punctiferalis*, *Diatraea grandiosella*, *Glyphodes pyloalis*, *Hellula undalis* and *Parapediasia teterrella*;
  (e) moths of the family Gelechiidae such as *Helcystogramma triannulella*, *Pectinophora gossypiella*, *Phthorimaea operculella* and *Sitotroga cerealella*;
  (f) moths of the family Geometridae such as *Ascotis selenaria*;
  (g) moths of the family Gracillariidae such as *Caloptilia theivora*, *Phyllocnistis citrella* and *Phyllonorycter ringoniella*;
  (h) butterflies of the family Hesperiidae such as *Parnara guttata*;
  (i) moths of the family Lasiocampidae such as *Malacosoma neustria*; (j) moths of the family Lymantriidae, for example, species belonging to the genus *Lymantria* (*Lymantria* spp.) such as *Lymantria dispar* and *Lymantria monacha*; and others such as *Euproctis pseudoconspersa* and *Orgyia thyellina*;
  (k) moths of the family Lyonetiidae, for example, species belonging to the genus *Lyonetia* (*Lyonetia* spp.) such as *Lyonetia clerkella* and *Lyonetia prunifoliella malinella*;
  (l) moths of the family Noctuidae, for example, species belonging to the genus *Spodoptera* (*Spodoptera* spp.) such as *Spodoptera depravata*, *Spodoptera eridania*, *Spodoptera exigua*, *Spodoptera frugiperda*, *Spodoptera littoralis* and *Spodoptera litura*; for example, species belonging to the genus *Autographa* (*Autographa* spp.) such as *Autographa gamma* and *Autographa nigrisigna*; for example, species belonging to the genus *Agrotis* (*Agrotis* spp.) such as *Agrotis ipsilon* and *Agrotis segetum*; for example, species belonging to the genus *Helicoverpa* (*Helicoverpa* spp.) such as *Helicoverpa armigera*, *Helicoverpa assulta* and *Helicoverpa zea*; for example, species belonging to the genus *Heliothis* (*Heliothis* spp.) such as *Heliothis armigera* and *Heliothis virescens*; and others such as *Aedia leucomelas*, *Ctenoplusia agnata*, *Eudocima tyrannus*, *Manmestra brassicae*, *Mythimna separata*, *Naranga aenescens*, *Panolis japonica*, *Peridroma saucia*, *Pseudoplusia includens* and *Tritoplusia ni*;
  (m) moths of the family Nolidae such as *Earias insulana*;
  (n) butterflies of the family Pieridae, for example, species belonging to the genus *Pieris* (*Pieris* spp.) such as *Pieris brassicae* and *Pieris rapae crucivora*;
  (o) moths of the family Plutellidae, for example, species belonging to the genus *Acrolepiopsis* (*Acrolepiopsis* spp.) such as *Acrolepiopsis sapporensis* and *Acrolepiopsis suzukiella*; and others such as *Plutella xylostella*;
  (p) moths of the family Pyralidae such as *Cadra cautella*, *Elasmopalpus lignosellus*, *Etiella zinckenella* and *Galleria mellonella*;
  (q) moths of the family Sphingidae, for example, species belonging to the genus *Manduca* (*Manduca* spp.) such as *Manduca quinquemaculata* and *Manduca sexta*;
  (r) moths of the family Stathmopodidae such as *Stathmopoda masinissa*;
  (s) moths of the family Tineidae such as *Tinea translucens*;
  (t) moths of the family Tortricidae, for example, species belonging to the genus *Adoxophyes* (*Adoxophyes* spp.) such as *Adoxophyes honmai* and *Adoxophyes orana*; for example, species belonging to the genus *Archips* (*Archips* spp.) such as *Archips breviplicanus* and *Archips fuscocupreanus*; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana* and *Sparganothis pilleriana*; and (u) moths of the family Yponomeutidae such as *Argyresthia conjugella*.

(2) Insect pests of the order Thysanoptera (a) pests of the family Phlaeothripidae such as *Ponticulothrips diospyrosi*; and (b) pests of the family Thripidae, for example, species belonging to the genus *Frankliniella* (*Frankliniella* spp.) such as *Frankliniella intonsa* and *Frankliniella occidentalis*; for example, species belonging to the genus *Thrips* (*Thrips* spp.) such as *Thrips palmi* and *Thrips tabaci*; and others such as *Heliothrips haemorrhoidalis* and *Scirtothrips dorsalis*.

(3) Insect Pests of the Order Hemiptera (A) Archaeorrhyncha (a) pests of the family Delphacidae such as *Laodelphax striatella, Nilaparvata lugens, Perkinsiella saccharicida* and *Sogatella furcifera*.

(B) Clypeorrhyncha (a) pests of the family Cicadellidae, for example, species belonging to the genus *Empoasca* (*Empoasca* spp.) such as *Empoasca fabae, Empoasca nipponica, Empoasca onukii* and *Empoasca sakaii*; and others such as *Arboridia apicalis, Balclutha saltuella, Epiacanthus stramineus, Macrosteles striifrons* and *Nephotettix cinctinceps*.

(C) Heteroptera (a) pests of the family Alydidae such as *Riptortus clavatus*;

(b) pests of the family Coreidae such as *Cletus punctiger* and *Leptocorisa chinensis*;

(c) pests of the family Lygaeidae such as *Blissus leucopterus, Cavelerius saccharivorus* and Togo *hemipterus*;

(d) pests of the family Miridae such as *Halticus insularis, Lygus lineolaris, Psuedatomoscelis seriatus, Stenodema sibiricum*, Stenotus rubrovittatus and Trigonotylus caelestialium;

(e) pests of the family Pentatomidae, for example, species belonging to the genus *Nezara* (*Nezara* spp.) such as *Nezara antennata* and *Nezara viridula*; for example, species belonging to the genus *Eysarcoris* (*Eysarcoris* spp.) such as *Eysarcoris aeneus, Eysarcoris lewisi* and *Eysarcoris ventralis*; and others such as *Dolycoris baccarum, Eurydema rugosum, Glaucias subpunctatus, Halyomorpha halys, Piezodorus hybneri, Plautia crossota* and *Scotinophora lurida*;

(f) pests of the family Pyrrhocoridae such as *Dysdercus cingulatus*;

(g) pests of the family Rhopalidae such as *Rhopalus msculatus*;

(h) pests of the family Scutelleridae such as *Eurygaster integriceps*; and (i) pests of the family Tingidae such as *Stephanitis nashi*.

(D) Sternorrhyncha (a) pests of the family Adelgidae such as *Adelges laricis*;

(b) pests of the family Aleyrodidae, for example, species belonging to the genus *Bemisia* (*Bemisia* spp.) such as *Bemisia argentifolii* and *Bemisia tabaci*; and others such as *Aleurocanthus spiniferus, Dialeurodes citri* and *Trialeurodes vaporariorum*;

(c) pests of the family Aphididae, for example, species belonging to the genus *Aphis* (*Aphis* spp.) such as *Aphis craccivora, Aphis fabae, Aphis forbesi, Aphis gossypii, Aphis pomi, Aphis sambuci* and *Aphis spiraecola*; for example, species belonging to the genus *Rhopalosiphum* (*Rhopalosiphum* spp.) such as *Rhopalosiphum maidis* and *Rhopalosiphum padi*; for example, species belonging to the genus *Dysaphis* (*Dysaphis* spp.) such as *Dysaphis plantaginea* and *Dysaphis radicola*; for example, species belonging to the genus *Macrosiphum* (*Macrosiphum* spp.) such as *Macrosiphum avenae* and *Macrosiphum euphorbiae*; for example, species belonging to the genus *Myzus* (*Myzus* spp.) such as *Myzus cerasi, Myzus persicae* and *Myzus varians*; and others such as *Acyrthosiphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodonhumuli, Schizaphis graminum, Sitobion avenae* and *Toxoptera aurantii*;

(d) pests of the family Coccidae, for example, species belonging to the genus *Ceroplastes* (*Ceroplastes* spp.) such as *Ceroplastes ceriferus* and *Ceroplastes rubens*;

(e) pests of the family Diaspididae, for example, species belonging to the genus *Pseudaulacaspis* (*Pseudaulacaspis* spp.) such as *Pseudaulacaspis pentagona* and *Pseudaulacaspis prunicola*; for example, species belonging to the genus *Unaspis* (*Unaspis* spp.) such as *Unaspis euonymi* and *Unaspis yanonensis*; and others such as *Aonidiella aurantii, Comstockaspis perniciosa, Fiorinia theae* and *Pseudaonidia paeoniae*;

(f) pests of the family Margarodidae such as *Drosicha corpulenta* and *Icerya purchasi*;

(g) pests of the family Phylloxeridae such as *Viteus vitifolii*;

(h) pests of the family Pseudococcidae, for example, species belonging to the genus *Planococcus* (*Planococcus* spp.) such as *Planococcus citri* and *Planococcus kuraunhiae*; and others such as *Phenacoccus solani* and *Pseudococcus comstocki*; and (i) pests of the family Psyllidae, for example, species belonging to the genus *Psylla* (*Psylla* spp.) such as *Psylla mali* and *Psylla pyrisuga*; and others such as *Diaphorina citri*.

(4) Insect Pests of the Suborder *Polyphaga*

(a) pests of the family Anobiidae such as *Lasioderma serricorne*;

(b) pests of the family Attelabidae such as *Byctiscus betulae* and *Rhynchites heros*;

(c) pests of the family Bostrichidae such as *Lyctus brunneus*;

(d) pests of the family Brentidae such as *Cylas formicarius*;

(e) pests of the family Buprestidae such as *Agrilus sinuatus*;

(f) pests of the family Cerambycidae such as *Anoplophora malasiaca, Monochamus alternatus, Psacothea hilaris* and *Xylotrechus pyrrhoderus*;

(g) pests of the family Chrysomelidae, for example, species belonging to the genus *Bruchus* (*Bruchus* spp.) such as *Bruchus pisorum* and *Bruchus rufimanus*; for example, species belonging to the genus *Diabrotica* (*Diabrotica* spp.) such as *Diabrotica barberi, Diabrotica undecimpunctata* and *Diabrotica virgifera*; for example, species belonging to the genus *Phyllotreta* (*Phyllotreta* spp.) such as *Phyllotreta nemorum* and *Phyllotreta striolata*; and others such as *Aulacophora femoralis, Callosobruchus chinensis, Cassida nebulosa, Chaetocnema concinna, Leptinotarsa decemlineata, Oulema oryzae* and *Psylliodes angusticollis*;

(h) pests of the family Coccinellidae, for example, species belonging to the genus *Epilachna* (*Epilachna* spp.) such as *Epilachna varivestis* and *Epilachna vigintioctopunctata*;

(i) pests of the family Curculionidae, for example, species belonging to the genus *Anthonomus* (*Anthonomus* spp.) such as *Anthonomus grandis* and *Anthonomus pomorum*; for example, species belonging to the genus *Sitophilus* (*Sitophilus* spp.) such as *Sitophilus granarius* and *Sitophilus zeamais*; and others such as *Echinocnemus squameus, Euscepes postfasciatus, Hylobius abietis, Hypera postica, Lissohoptrus oryzophilus, Otiorhynchus sulcatus, Sitona lineatus* and *Sphenophorus venatus;*

(j) pests of the family Elateridae, for example, species belonging to the genus *Melanotus* (*Melanotus* spp.) such as *Melanotus fortnumi* and *Melanotus tamsuyensis;*

(k) pests of the family Nitidulidae such as *Epuraea domina;*

(l) pests of the family Scarabaeidae, for example, species belonging to the genus *Anomala* (*Anomala* spp.) such as *Anomala cuprea* and *Anomala rufocuprea*; and others such as *Cetonia aurata, Gametis jucunda, Heptophylla picea, Melolontha* and *Popillia japonica;*

(m) pests of the family Scolytidae such as *Ips typographus;*

(n) pests of the family Staphylinidae such as *Paederus fuscipes;*

(o) pests of the family Tenebrionidae such as *Tenebrio molitor* and *Tribolium castaneum*; and (p) pests of the family Trogossitidae such as *Tenebroides mauritanicus.*

(5) Insect Pests of the Order Diptera (A) Brachycera (a) pests of the family Agromyzidae, for example, species belonging to the genus *Liriomyza* (*Liriomyza* spp.) such as *Liriomyza bryoniae, Liriomyza chinensis, Liriomyza sativae* and *Liriomyza trifolii*; and others such as *Chromatomyia horticola* and *Agromyza oryzae;*

(b) pests of the family Anthomyiidae, for example, species belonging to the genus *Delia* (*Delia* spp.) such as *Delia platura* and *Delia radicum*; and others such as *Pegomya cunicularia;*

(c) pests of the family Drosophilidae, for example, species belonging to the genus *Drosophila* (*Drosophila* spp.) such as *Drosophila melanogaster* and *Drosophila suzukii;*

(d) pests of the family Ephydridae such as *Hydrellia griseola;*

(e) pests of the family Psilidae such as *Psila rosae*; and (f) pests of the family Tephritidae, for example, species belonging to the genus *Bactrocera* (*Bactrocera* spp.) such as *Bactrocera cucurbitae* and *Bactrocera dorsalis*; for example, species belonging to the genus *Rhagoletis* (*Rhagoletis* spp.) such as *Rhagoletis cerasi* and *Rhagoletis pomonella*; and others such as *Ceratitis capitata* and *Dacus oleae.*

(B) Nematocera (a) pests of the family Cecidomyiidae such as *Asphondylia yushimai, Contarinia sorghicola, Mayetiola destructor* and *Sitodiplosis mosellana.*

(6) Insect Pests of the Order Orthoptera (a) pests of the family Acrididae, for example, species belonging to the genus *Schistocerca* (*Schistocerca* spp.) such as *Schistocerca americana* and *Schistocerca gregaria*; and others such as *Chortoicetes terminifera, Dociostaurus maroccanus, Locusta migratoria, Locustana pardalina, Nomadacris septemfasciata* and *Oxya yezoensis;*

(b) pests of the family Gryllidae such as *Acheta domestica* and *Teleogryllus emma;*

(c) pests of the family Gryllotalpidae such as *Gryllotalpa orientalis*; and (d) pests of the family Tettigoniidae such as *Tachycines asynamorus.*

(7) Mites and Ticks (Acari)

(A) Acaridida of the Order Astigmata (a) mites and ticks of the family Acaridae, for example, species belonging to the genus *Rhizoglyphus* (*Rhizoglyphus* spp.) such as *Rhizoglyphus echinopus* and *Rhizoglyphus robini*; for example, species belonging to the genus *Tyrophagus* (*Tyrophagus* spp.) such as *Tyrophagus neiswanderi, Tyrophagus perniciosus, Tyrophagus putrescentiae* and *Tyrophagus similis*; and others such as *Acarus siro, Aleuroglyphus ovatus* and *Mycetoglyphus fungivorus;*

(B) Actinedida of the Order Prostigmata (a) mites and ticks of the family Tetranychidae, for example, species belonging to the genus *Bryobia* (*Bryobia* spp.) such as *Bryobia praetiosa* and *Bryobia rubrioculus;* for example, species belonging to the genus *Eotetranychus* (*Eotetranychus* spp.) such as *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus*; for example, species belonging to the genus *Oligonychus* (*Oligonychus* spp.) such as *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii* and *Oligonychus ununguis*; for example, species belonging to the genus *Panonychus* (*Panonychus* spp.) such as *Panonychus citri, Panonychus mori* and *Panonychus ulmi*; for example, species belonging to the genus *Tetranychus* (*Tetranychus* spp.) such as *Tetranychus cinnabarinus, Tetranychus kanzawai, Tetranychus ludeni, Tetranychus quercivorus, Tetranychus phaselus, Tetranychus urticae, Tetranychus viennensis* and *Tetranychus evansi*; for example, species belonging to the genus *Aponychus* (*Aponychus* spp.) such as *Aponychus corpuzae* and *Aponychus firmianae*; for example, species belonging to the genus *Sasanychus* (*Sasanychus* spp.) such as *Sasanychus akitanus* and *Sasanychus pusillus*; for example, species belonging to the genus *Shizotetranychus* (*Shizotetranychus* spp.) such as *Shizotetranychus celarius, Shizotetranychus longus, Shizotetranychus miscanthi, Shizotetranychus recki* and *Shizotetranychus schizopus*; and others such as *Tetranychina harti, Tuckerella pavoniformis* and *Yezonychus sapporensis;*

(b) mites and ticks of the family Tenuipalpidae, for example, species belonging to the genus *Brevipalpus* (*Brevipalpus* spp.) such as *Brevipalpus lewisi, Brevipalpus obovatus, Brevipalpus phoenicis, Brevipalpus russulus* and *Brevipalpus californicus*; for example, species belonging to the genus *Tenuipalpus* (*Tenuipalpus* spp.) such as *Tenuipalpus pacificus* and *Tenuipalpus zhizhilashviliae*; and others such as *Dolichotetranychus floridanus;*

(c) mites and ticks of the family Eriophyidae, for example, species belonging to the genus *Aceria* (*Aceria* spp.) such as *Aceria diospyri, Aceria ficus, Aceria japonica, Aceria kuko, Aceria paradianthi, Aceria tiyingi, Aceria tulipae* and *Aceria zoysiea*; for example, species belonging to the genus *Eriophyes* (*Eriophyes* spp.) such as *Eriophyes chibaensis* and *Eriophyes emarginatae*; for example, species belonging to the genus *Aculops* (*Aculops* spp.) such as *Aculops lycopersici* and *Aculops pelekassi*; for example, species belonging to the genus *Aculus* (*Aculus* spp.) such as *Aculus fockeui* and *Aculus schlechtendali*; and others such as *Acaphylla theavagrans, Calacarus carinatus, Colomerus vitis, Calepitrimerus vitis, Epitrimerus pyri, Paraphytoptus kikus, Paracalacarus podocarpi* and *Phyllocotruta citri*;

(d) mites and ticks of the family Transonemidae, for example, species belonging to the genus *Tarsonemus* (*Tarsonemus* spp.) such as *Tarsonemus bilobatus* and *Tarsonemus waitei*; and others such as *Phytonemus pallidus* and *Polyphagotarsonemus latus*; and (e) mites and ticks of the family Penthaleidae, for example, species belonging to the genus *Penthaleus* (*Penthaleus* spp.) such as *Penthaleus erythrocephalus* and *Penthaleus major*.

The pest control agent of the present invention may be mixed with or used in combination with other active ingredients such as fungicides, insecticidal and acaricidal agents, nematicides and soil pesticides; plant regulators, synergists, fertilizers, soil conditioners, animal feeds and the like.

A combination of the heteroaryl pyrimidine compound of the present invention and other active ingredients can be expected to have a synergistic effect on insecticidal, acaricidal and nematicidal activities. The synergistic effect can be confirmed by the Colby's formula (Colby, S. R.; Calculating Synergistic and Antagonistic Responses of Herbicide Combinations; Weeds 15, pp. 20-22, 1967) according to a conventional method.

Specific examples of insecticidal/acaricidal agents, nematicides, soil pesticides, anthelmintics and the like which can be mixed with or used in combination with the pest control agent of the present invention are shown below.

(1) Acetylcholinesterase inhibitors:
(a) carbamate-based inhibitors: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam-sodium, promecarb;
(b) organophosphorus-based inhibitors: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemetonmethyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion, bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, sulprofos.

(2) GABA-gated chloride channel antagonists: acetoprole, chlordane, endosulfan, ethiprole, fipronil, pyrafluprole, pyriprole; camphechlor, heptachlor, dienochlor.

(3) Sodium channel modulators: acrinathrin, d-cis/trans allethrin, d-trans allethrin, bifenthrin, bioallethrin, bioallethrin S-cyclopentyl isomers, bioresmethrin, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ζ-cypermethrin, cyphenothrin [(1R)-trans isomers], deltamethrin, empenthrin [(EZ)-(1R)-isomers], esfenvalerate, etofenprox, fenpropathrin, fenvalerate, flucythrinate, flumethrin, τ-fluvalinate, halfenprox, imiprothrin, kadethrin, permethrin, phenothrin [(1R)-trans isomers], prallethrin, pyrethrum, resmethrin, silafluofen, tefluthrin, tetramethrin [(1R)-isomers], tralomethrin, transfluthrin, allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone, flupyrimine.

(5) Nicotinic acetylcholine receptor allosteric modulators: spinetoram, spinosad.

(6) Chloride channel activators: abamectin, emamectin-benzoate, lepimectin, milbemectin, ivermectin, selamectin, doramectin, eprinomectin, moxidectin, milbemycin, milbemycin oxime, nemadectin.

(7) Juvenile hormone analogues: hydroprene, kinoprene, methoprene, fenoxycarb, pyriproxyfen, diofenolan, epofenonane, triprene.

(8) Other nonspecific inhibitors: methyl bromide, chloropicrin, sulfuryl fluoride, borax, tartar emetic.

(9) Homoptera selective antifeedants: flonicamid, pymetrozine, pyrifluquinazon.

(10) Mite growth inhibitors: clofentezine, diflovidazin, hexythiazox, etoxazole.

(11) Insect midgut inner membrane disrupting agents derived from microorganisms: *Bacillus thuringiensis* subsp. *israelensi, Bacillus sphaericus, Bacillus thuringiensis* subsp. *aizawai, Bacillus thuringiensis* subsp. *kurstaki, Bacillus thuringiensis* subsp. *tenebrionis*, Bt crop proteins: Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondrial ATP biosynthetic enzyme inhibitors: diafenthiuron, azocyclotin, cyhexatin, fenbutatin oxide, propargite, tetradifon.

(13) Oxidative phosphorylation uncouplers: chlorfenapyr, sulfluramid, DNOC, binapacryl, dinobuton, dinocap.

(14) Nicotinic acetylcholine receptor channel blockers: bensultap, cartap hydrochloride, nereistoxin, thiosultap-sodium, thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron.

(16) Diptera molting disrupting agents: cyromazine.

(17) Molting hormone receptor agonists: chromafenozide, halofenozide, methoxyfenozide, tebufenozide.

(18) Octopamine receptor agonists: amitraz, demiditraz, chlordimeform.

(19) Mitochondrial electron transport system complex III inhibitors: acequinocyl, fluacrypyrim, hydramethylnon.

(20) Mitochondrial electron transport system complex I inhibitors: fenazaquin, fenpyroximate, pyrimidifen, pyridaben, tebufenpyrad, tolfenpyrad, rotenone.

(21) Voltage-dependent sodium channel blockers: indoxacarb, metaflumizone.

(22) Acetyl CoA carboxylase inhibitors: spirodiclofen, spiromesifen, spirotetramat.

(23) Mitochondrial electron transport system complex IV inhibitors: aluminum phosphide, calcium phosphide, phosphine, zinc phosphide, cyanide.

(24) Mitochondrial electron transport system complex II inhibitors: cyenopyrafen, cyflumetofen, pyflubumide.

(25) Ryanodine receptor modulators: chlorantraniliprole, cyantraniliprole, flubendiamide, cyclaniliprole, tetraniliprole.

(26) Mixed function oxidase inhibitor compounds: piperonyl butoxide.

(27) Latrophilin receptor agonists: depsipeptide, cyclodepsipeptide, 24-membered cyclodepsipeptide, emodepside.

(28) Other agents (with unknown action mechanisms): azadirachtin, benzoximate, bifenazate, bromopropylate, quinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure japonilure, metoxadiazone, oil, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl) benzonitrile (CAS: 943137-49-3), broflanilide, other meta-diamides, Steinernema carpocapsae, Steinernema glaseri, Pasteuria *penetrans*, *Paecilomyces tenuipes*, *Paecilomyces fumosoroseus*, *Beauveria bassiana*, *Beauveria brongniartii*, *Metarhizium anisopliae*, *Verticillium* lecanii.

(29) Anthelmintics:
 (a) benzimidazole-based anthelmintics: fenbendazole, albendazole, triclabendazole, oxibendazole, mebendazole, oxfendazole, parbendazole, flubendazole, febantel, netobimin, thiophanate, thiabendazole, cambendazole;
 (b) salicylanilide-based anthelmintics: closantel, oxyclozanide, rafoxanide, niclosamide;
 (c) substituted phenol-based anthelmintics: nitroxinil, nitroscanate;
 (d) pyrimidine-based anthelmintics: pyrantel, morantel;
 (e) imidazothiazole-based anthelmintics: levamisole, tetramisole;
 (f) tetrahydropyrimidine-based anthelmintics: praziquantel, epsiprantel; and
 (g) other anthelmintics: cyclodiene, ryania, clorsulon, metronidazole, demiditraz, piperazine, diethylcarbamazine, dichlorophen, monepantel, tribendimidine, amidantel, thiacetarsamide, melarsomine, arsenamide.

Specific examples of the fungicide which can be mixed with or used in combination with the pest control agent of the present invention are shown below.

(1) Nucleic Acid Biosynthesis Inhibitors:
 (a) RNA polymerase I inhibitors: benalaxyl, benalaxyl-M, furalaxyl, metalaxyl, metalaxyl-M, oxadixyl, clozylacon, ofurace;
 (b) adenosine deaminase inhibitors: bupirimate, dimethirimol, ethirimol;
 (c) DNA/RNA synthesis inhibitors: hymexazol, octhilinone;
 (d) DNA topoisomerase II inhibitors: oxolinic acid.

(2) Mitotic Inhibitors and Cell Division Inhibitors:
 (a) β-tubulin polymerization inhibitors: benomyl, carbendazim, chlorfenazole, fuberidazole, thiabendazole, thiophanate, thiophanate-methyl, diethofencarb, zoxamide, ethaboxam;
 (b) cell division inhibitors: pencycuron;
 (c) delocalization inhibitors of spectrin-like protein: fluopicolide.

(3) Respiration Inhibitors:
 (a) complex I NADH oxidoreductase inhibitors: diflumetorim, tolfenpyrad;
 (b) complex II succinate dehydrogenase inhibitors: benodanil, flutolanil, mepronil, isofetamid, fluopyram, fenfuram, furmecyclox, carboxin, oxycarboxin, thifluzamide, benzovindiflupyr, bixafen, fluxapyroxad, furametpyr, isopyrazam, penflufen, penthiopyrad, sedaxane, boscalid, pyraziflumid;
 (c) complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoxim-methyl, trifloxystrobin, dimoxystrobin, fenaminstrobin, metominostrobin, orysastrobin, famoxadone, fluoxastrobin, fenamidone, pyribencarb, mandestrobin;
 (d) complex III ubiquinol reductase Qi inhibitors: cyazofamid, amisulbrom;
 (e) oxidative phosphorylation uncouplers: binapacryl, meptyldinocap, dinocap, fluazinam, ferimzone;
 (f) oxidative phosphorylation inhibitors (ATP synthase inhibitors): fentin acetate, fentin chloride, fentin hydroxide;
 (g) ATP production inhibitor: silthiofam;
 (h) complex III: Qx (unknown) inhibitors of cytochrome bc1 (ubiquinone reductase): ametoctradin.

(4) Amino Acid and Protein Synthesis Inhibitors
 (a) methionine biosynthesis inhibitors: andoprim, cyprodinil, mepanipyrim, pyrimethanil;
 (b) protein synthesis inhibitors: blasticidin S, kasugamycin, kasugamycin hydrochloride, streptomycin, oxytetracycline.

(5) Signal Transduction Inhibitors:
 (a) signal transduction inhibitors: quinoxyfen, proquinazid;
 (b) MAP/histidine kinase inhibitors in osmotic signal transduction: fenpiclonil, fludioxonil, chlozolinate, iprodione, procymidone, vinclozolin.

(6) Lipid and Cell Membrane Synthesis Inhibitors:
 (a) phospholipid biosynthesis and methyltransferase inhibitors: edifenphos, iprobenfos, pyrazophos, isoprothiolane;
 (b) lipid peroxidants: biphenyl, chloroneb, dicloran, quintozene, tecnazene, tolclofos-methyl, etridiazole;
 (c) agents acting on cell membranes: iodocarb, propamocarb, propamocarb hydrochloride, propamocarb-fosetylate, prothiocarb;
 (d) microorganisms disturbing pathogenic cell membranes: *Bacillus subtilis, Bacillus subtilis* strain QST713, *Bacillus subtilis* strain FZB24, *Bacillus subtilis* strain MBI600, *Bacillus subtilis* strain D747, *Bacillus amyloliquefaciens*;

(e) agents disturbing cell membranes: extracts of *Melaleuca alternifolia* (tea tree).

(7) Sterol Biosynthesis Inhibitors of Cell Membranes:
  (a) C14 demethylation inhibitors in sterol biosynthesis: triforine, pyrifenox, pyrisoxazole, fenarimol, flurprimidol, nuarimol, imazalil, imazalil sulfate, oxpoconazole fumarate, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, furconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole, prothioconazole, voriconazole, mefentrifluconazole;
  (b) inhibitors of Δ14 reductase and Δ8→Δ7-isomerase in sterol biosynthesis: aldimorph, dodemorph, dodemorph acetate, fenpropimorph, tridemorph, fenpropidin, piperalin, spiroxamine;
  (c) 3-keto reductase inhibitors in C4 demethylation in sterol biosynthesis system: fenhexamid, fenpyrazamine;
  (d) squalene epoxidase inhibitors in sterol biosynthesis system: pyributicarb, naftifine, terbinafine.

(8) Cell Wall Synthesis Inhibitors
  (a) trehalase inhibitors: validamycin;
  (b) chitin synthase inhibitors: polyoxins, polyoxorim;
  (c) cellulose synthase inhibitors: dimethomorph, flumorph, pyrimorph; benchthiavalicarb-isopropyl, iprovalicarb, tolprocarb, valifenalate, mandipropamid.

(9) Melanin Biosynthesis Inhibitors
  (a) reductase inhibitors in melanin biosynthesis: fthalide, pyroquilon, tricyclazole;
  (b) anhydrase inhibitors in melanin biosynthesis: carpropamid, diclocymet, fenoxanil;

(10) Resistance Inducers of Host Plants:
  (a) agents acting on salicylic acid synthetic pathway: acibenzolar-S-methyl;
  (b) other agents: probenazole, tiadinil, isotianil, laminarin, *Reynoutria sachalinensis* extract.

(11) Agents with Unknown Actions:
  cymoxanil, fosetyl-aluminium, phosphoric acid (phosphates), tecloftalam, triazoxide, flusulfamide, diclomezine, methasulfocarb, cyflufenamid, metrafenone, pyriofenone, dodine, dodine free base, flutianil.

(12) Agents Having Multiple Points of Action:
  copper (copper salts), Bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine acetates (iminoctadine triacetate), iminoctadine albesilates (iminoctadine trialbesilate), anilazine, dithianon, quinomethionate, fluoroimide.

(13) Other Agents:
  DBEDC, fluorfolpet, guazatine acetate, bis(8-quinolinolato) copper (II), propamidine, chloropicrin, cyprofuram, *agrobacterium*, bethoxazin, diphenylamine, methyl isothiocyanate (MITC), mildiomycin, capsaicin, cufraneb, cyprosulfamide, dazomet, debacarb, dichlorophen, flumetover, fosetyl-calcium, fosetyl-sodium, irumamycin, natamycin, nitrothal-isopropyl, oxamocarb, pyrrolnitrin, tebufloquin, tolnifanide, zarilamide, algophase, amicarthiazol, oxathiapiprolin, metiram zinc, benthiazole, trichlamide, uniconazole, oxyfenthiin, picarbutrazox, fenpicoxamid, dichlobentiazox, quinofumelin, thiuram, ambam, *Agrobacterium radiobacter, Coniothyrium minitans, Pseudomonas fluorescens, Pseudomonas rhodesiae, Talaromyces flavus, Trichoderma atroviride, Erwinia carotovora* subsp. *carotovora, Bacillus simplex, Variovorax paradoxus, Lactobacillus plantarum.*

Specific examples of plant regulators which can be mixed with or used in combination with the pest control agent of the present invention are shown below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3, 1-methylcyclopropane, N-acetyl aminoethoxyvinyl glycine (aka: aviglycine), aminooxyacetate, silver nitrate, cobalt chloride, IAA, 4-CPA, cloprop, 2,4-D, MCPB, indole-3-butyrate, dichlorprop, phenothiol, 1-naphthylacetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl) aminobutyric acid, ethephon, chlormequat, mepiquat chloride, benzyl adenine, 5-aminolevulinic acid, daminozide.

[Ectoparasite Control Agent]

The ectoparasite control agent of the present invention contains at least one selected from the heteroaryl pyrimidine compounds of the present invention as an active ingredient. The amount of the heteroaryl pyrimidine compound contained in the ectoparasite control agent of the present invention is not particularly limited as long as it shows the effect of controlling ectoparasites.

Examples of host animals to be treated with the ectoparasite control agent of the present invention include warm-blooded animals such as humans, domestic mammals (for example, cattle, horses, pigs, sheep, goats and the like), laboratory animals (for example, mice, rats, gerbils and the like), pet animals (for example, hamsters, guinea pigs, dogs, cats, horses, squirrels, rabbits, ferrets, and the like), wild and zoo mammals (monkeys, foxes, deer, buffaloes and the like), domestic fowls (turkeys, ducks, chickens, quails, geese and the like) and pet birds (pigeons, parrots, hill mynas, Java sparrows, parakeets, society finches, canaries and the like); or fish such as salmon, trout and nishikigoi. In addition, honey bees, stag beetles and beetles can be exemplified.

The ectoparasite control agent of the present invention can be applied by a known veterinary method (topical, oral, parenteral or subcutaneous administration). As a method therefor, a method of orally administering tablets, capsules, mixed feeds or the like to the animals; a method of administering to the animals by using an immersion liquid, suppository, injection (intramuscular, subcutaneous, intravenous, intraperitoneal or the like) or the like; a method of topically administering by spraying, pouring-on or spotting-on an oily or aqueous liquid preparation; a method of kneading an ectoparasite control agent in a resin, molding the kneaded product into an appropriate shape such as a collar, ear tag or the like, and attaching and topically administering the resultant to the animals; and the like can be mentioned.

Ectoparasites are parasitic in and on host animals, especially warm-blooded animals. More specifically, the ectoparasites are parasitic in and on the back, armpit, lower abdomen, inner thigh and the like of the host animals and obtain nutritional sources such as blood and dandruff from the animals to live. Examples of ectoparasites include mites and ticks, lice, fleas, mosquitoes, stable flies, flesh flies and the like. Specific examples of the ectoparasites which can be controlled by the ectoparasite control agent of the present invention are shown below.
(1) Mites and Ticks (Acari)

Mites and ticks belonging to the family Dermanyssidae, mites and ticks belonging to the family Macronyssidae, mites and ticks belonging to the family Laelapidae, mites and ticks belonging to the family Varroidae, mites and ticks belonging to the family Argasidae, mites and ticks belonging to the family Ixodidae, mites and ticks belonging to the family Psoroptidae, mites and ticks belonging to the family Sarcoptidae, mites and ticks belonging to the family Knemidokoptidae, mites and ticks belonging to the family Demodixidae, mites and ticks belonging to the family Trombiculidae, insect-parasitic mites and ticks such as *Coleopterophagus berlesei* or the like.
(2) Phthiraptera Lice belonging to the family Haematopinidae, lice belonging to the family Linognathidae, chewing lice belonging to the family Menoponidae, chewing lice belonging to the family Philopteridae, chewing lice belonging to the family Trichodectidae;
(3) Siphonaptera Fleas of the family Pulicidae, for example, species belonging to the genus *Ctenocephalides* (*Ctenocephalides* spp.) such as *Ctenocephalides canis* and *Ctenocephalides felis*;
 fleas belonging to the family Tungidae, fleas belonging to the family Ceratophyllidae, fleas belonging to the family Leptopsyllidae.
(4) Hemiptera
(5) Insect Pests of the Order Diptera Mosquitoes belonging to the family Culicidae, black flies belonging to the family Simuliidae, biting midges belonging to the family Ceratopogonidae, horseflies belonging to the family Tabanidae, flies belonging to the family Muscidae, tsetse flies belonging to the family Glossinidae; flesh flies belonging to the family Sarcophagidae, flies belonging to the family Hippoboscidae, flies belonging to the family Calliphoridae, flies belonging to the family Oestridae.

[Endoparasite Control- or Endoparasite-Expelling Agent]

The endoparasite control- or endoparasite-expelling agent of the present invention contains at least one selected from the heteroaryl pyrimidine compounds of the present invention as an active ingredient. The amount of the heteroaryl pyrimidine compound contained in the endoparasite control- or endoparasite-expelling agent of the present invention is not particularly limited as long as it shows the effect of controlling endoparasites.

The parasite to be targeted by the endoparasite control- or endoparasite-expelling agent of the present invention is parasitic (endoparasitic) in host animals, especially warm blooded animals and fish. Examples of host animals for which the endoparasite control- or endoparasite-expelling agent of the present invention is effective include warm-blooded animals such as humans, domestic mammals (for example, cattle, horses, pigs, sheep, goats and the like), laboratory animals (for example, mice, rats, gerbils and the like), pet animals (for example, hamsters, guinea pigs, dogs, cats, horses, squirrels, rabbits, ferrets, and the like), wild and zoo mammals (monkeys, foxes, deer, buffaloes and the like), domestic fowls (turkeys, ducks, chickens, quails, geese and the like) and pet birds (pigeons, parrots, hill mynas, Java sparrows, parakeets, society finches, *canaries* and the like); or fish such as salmon, trout and nishikigoi. By controlling and expelling parasites, it is possible to prevent or treat parasitic diseases mediated by the parasites.

Examples of the parasites to be controlled or exterminated include the followings.
(1) Nematodes of the order Dioctophymatida
 (a) kidney worms of the family Dioctophymatidae, for example, species belonging to the genus *Dioctophyma* (*Dioctophyma* spp.) such as *Dioctophyma renale*; and
 (b) kidney worms of the family Soboliphymatidae, for example, species belonging to the genus *Soboliphyme* (*Soboliphyme* spp.) such as *Soboliphyme abei* and *Soboliphyme baturini*.
(2) Nematodes of the order Trichocephalida
 (a) trichina worms of the family Trichinellidae, for example, species belonging to the genus *Trichinella* (*Trichinella* spp.) such as *Trichinella spiralis*; and
 (b) whipworms of the family Trichuridae, for example, species belonging to the genus *Capillaria* (*Capillaria* spp.) such as *Capillaria annulata, Capillaria contorta, Capillaria hepatica, Capillaria perforans, Capillaria plica*, and *Capillaria suis*; and species belonging to the genus *Trichuris* (*Trichuris* spp.) such as *Trichuris vulpis, Trichuris discolor, Trichuris ovis, Trichuris skrjabini*, and *Trichuris suis*.
(3) Nematodes of the Order Rhabditida
 threadworms of the family Strongyloididae, for example, species belonging to the genus *Strongyloides* (*Strongyloides* spp.) such as *Strongyloides papillosus, Strongyloides planiceps, Strongyloides ransomi, Strongyloides suis, Strongyloides stercoralis, Strongyloides tumefaciens*, and *Strongyloides ratti*.
(4) Nematodes of the Order Strongylida
 hookworms of the family Ancylostomatidae, for example, species belonging to the genus *Ancylostoma* (*Ancylostoma* spp.) such as *Ancylostoma braziliense, Ancylostoma caninum, Ancylostoma duodenale*, and *Ancylostoma tubaeforme*; species belonging to the genus *Uncinaria* (*Uncinaria* spp.) such as *Uncinaria stenocephala*; and species belonging to the genus *Bunostomum* (*Bunostomum* spp.) such as *Bunostomum phlebotomum* and *Bunostomum trigonocephalum*.
(5) Nematodes of the Order Strongylida
 (a) nematodes of the family Angiostrongylidae, for example, species belonging to the genus *Aelurostrongylus* (*Aelurostrongylus* spp.) such as *Aelurostrongylus abstrusus*; and species belonging to the genus *Angiostrongylus* (*Angiostrongylus* spp.) such as *Angiostrongylus vasorum* and *Angiostrongylus cantonesis*;
 (b) nematodes of the family Crenosomatidae, for example, species belonging to the genus *Crenosoma* (*Crenosoma* spp.) such as *Crenosoma aerophila* and *Crenosoma vulpis*;
 (c) nematodes of the family Filaroididae, for example, species belonging to the genus *Filaroides* (*Filaroides* spp.) such as *Filaroides hirthi* and *Filaroides osleri*;
 (d) lungworms of the family Metastrongylidae, for example, species belonging to the genus *Metastrongylus* (*Metastrongylus* spp.) such as *Metastrongylus apri, Metastrongylus asymmetricus, Metastrongylus pudendotectus* and *Metastrongylus salmi*; and
 (e) gapeworms of the family Syngamidae, for example, species belonging to the genus *Cyathostoma* (*Cyathostoma* spp.) such as *Cyathostoma bronchialis*; and species belonging to the genus *Syngamus* (*Syngamus* spp.) such as *Syngamus skrjabinomorpha* and *Syngamus trachea*.

(6) Nematodes of the Order Strongylida
 (a) nematodes of the family Molineidae, for example, species belonging to the genus *Nematodirus* (*Nematodirus* spp.) such as *Nematodirus filicollis* and *Nematodirus spathiger*;
 (b) nematodes of the family Dictyocaulidae, for example, species belonging to the genus *Dictyocaulus* (*Dictyocaulus* spp.) such as *Dictyocaulus filaria* and *Dictyocaulus viviparus*;
 (c) nematodes of the family Haemonchidae, for example, species belonging to the genus *Haemonchus* (*Haemonchus* spp.) such as *Haemonchus contortus*; and species belonging to the genus *Mecistocirrus* (*Mecistocirrus* spp.) such as *Mecistocirrus digitatus*;
 (d) nematodes of the family Haemonchidae, for example, species belonging to the genus *Ostertagia* (*Ostertagia* spp.) such as *Ostertagia ostertagi*;
 (e) nematodes of the family Heligmonellidae, for example, species belonging to the genus *Nippostrongylus* (*Nippostrongylus* spp.) such as *Nippostrongylus braziliensis*; and
 (f) nematodes of the family Trichostrongylidae, for example, species belonging to the genus *Trichostrongylus* (*Trichostrongylus* spp.) such as *Trichostrongylus axei*, *Trichostrongylus colubriformis* and *Trichostrongylus tenuis*; species belonging to the genus *Hyostrongylus* (*Hyostrongylus* spp.) such as *Hyostrongylus rubidus*; and species belonging to the genus *Obeliscoides* (*Obeliscoides* spp.) such as *Obeliscoides cuniculi*.

(7) Nematodes of the Order Strongylida
 (a) nematodes of the family Chabertiidae, for example, species belonging to the genus *Chabertia* (*Chabertia* spp.) such as *Chabertia ovina*; and species belonging to the genus *Oesophagostomum* (*Oesophagostomum* spp.) such as *Oesophagostomum brevicaudatum*, *Oesophagostomum columbianum*, *Oesophagostomum dentatum*, *Oesophagostomum georgianum*, *Oesophagostomum maplestonei*, *Oesophagostomum quadrispinulatum*, *Oesophagostomum radiatum*, *Oesophagostomum venulosum* and *Oesophagostomum watanabei*;
 (b) nematodes of the family Stephanuridae, for example, species belonging to the genus *Stephanurus* (*Stephanurus* spp.) such as *Stephanurus dentatus*; and
 (c) nematodes of the family Strongylidae, for example, species belonging to the genus *Strongylus* (*Strongylus* spp.) such as *Strongylus asini*, *Strongylus edentatus*, *Strongylus equinus* and *Strongylus vulgaris*.

(8) Nematodes of the order Oxyurida
 nematodes of the family Oxyuridae, for example, species belonging to the genus *Enterobius* (*Enterobius* spp.) such as *Enterobius anthropopitheci* and *Enterobius vermicularis*; species belonging to the genus *Oxyuris* (*Oxyuris* spp.) such as *Oxyuris equi*; and species belonging to the genus *Passalurus* (*Passalurus* spp.) such as *Passalurus ambiguus*.

(9) Nematodes of the Order Ascaridida
 (a) nematodes of the family Ascaridiidae, for example, species belonging to the genus *Ascaridia* (*Ascaridia* spp.) such as *Ascaridia galli*;
 (b) nematodes of the family Heterakidae, for example, species belonging to the genus *Heterakis* (*Heterakis* spp.) such as *Heterakis beramporia*, *Heterakis brevispiculum*, *Heterakis gallinarum*, *Heterakis pusilla* and *Heterakis putaustralis*;
 (c) nematodes of the family Anisakidae, for example, species belonging to the genus *Anisakis* (*Anisakis* spp.) such as *Anisakis simplex*;
 (d) nematodes of the family Ascarididae, for example, species belonging to the genus *Ascaris* (*Ascaris* spp.) such as *Ascaris lumbricoides* and *Ascaris suum*; and species belonging to the genus *Parascaris* (*Parascaris* spp.) such as *Parascaris equorum*; and
 (e) nematodes of the family Toxocaridae, for example, species belonging to the genus *Toxocara* (*Toxocara* spp.) such as *Toxocara canis*, *Toxocara leonina*, *Toxocara suum*, *Toxocara vitulorum* and *Toxocara cati*.

(10) Nematodes of the order Spirurida
 (a) nematodes of the family Onchocercidae, for example, species belonging to the genus *Brugia* (*Brugia* spp.) such as *Brugia malayi*, *Brugia pahangi* and *Brugia patei*; species belonging to the genus *Dipetalonema* (*Dipetalonema* spp.) such as *Dipetalonema reconditum*; species belonging to the genus *Dirofilaria* (*Dirofilaria* spp.) such as *Dirofilaria immitis*; species belonging to the genus *Filaria* (*Filaria* spp.) such as *Filaria oculi*; and species belonging to the genus *Onchocerca* (*Onchocerca* spp.) such as *Onchocerca cervicalis*, *Onchocerca gibsoni* and *Onchocerca gutturosa*;
 (b) nematodes of the family Setariidae, for example, species belonging to the genus *Setaria* (*Setaria* spp.) such as *Setaria digitata*, *Setaria equina*, *Setaria labiatopapillosa* and *Setaria marshalli*; and species belonging to the genus *Wuchereria* (*Wuchereria* spp.) such as *Wuchereria bancrofti*; and
 (c) nematodes of the family Filariidae, for example, species belonging to the genus *Parafilaria* (*Parafilaria* spp.) such as *Parafilaria multipapillosa*; and species belonging to the genus *Stephanofilaria* (*Stephanofilaria* spp.) such as *Stephanofilaria assamensis*, *Stephanofilaria dedoesi*, *Stephanofilaria kaeli*, *Stephanofilaria okinawaensis* and *Stephanofilaria stilesi*.

(11) Nematodes of the Order Spirurida
 (a) nematodes of the family Gnathostomatidae, for example, species belonging to the genus *Gnathostoma* (*Gnathostoma* spp.) such as *Gnathostoma doloresi* and *Gnathostoma spinigerum*;
 (b) nematodes of the family Habronematidae, for example, species belonging to the genus *Habronema* (*Habronema* spp.) such as *Habronema majus*, *Habronema microstoma* and *Habronema muscae*; and species belonging to the genus *Draschia* (*Draschia* spp.) such as *Draschia megastoma*;
 (c) nematodes of the family Physalopteridae, for example, species belonging to the genus *Physaloptera* (*Physaloptera* spp.) such as *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica* and *Physaloptera vulpineus*;
 (d) nematodes of the family Gongylonematidae, for example, species belonging to the genus *Gongylonema* (*Gongylonema* spp.) such as *Gongylonema pulchrum*;
 (e) nematodes of the family Spirocercidae, for example, species belonging to the genus *Ascarops* (*Ascarops* spp.) such as *Ascarops strongylina*; and
 (f) nematodes of the family Thelaziidae, for example, species belonging to the genus *Thelazia* (*Thelazia* spp.) such as *Thelazia callipaeda*, *Thelazia gulosa*, *Thelazia lacrymalis*, *Thelazia rhodesi* and *Thelazia skrjabini*.

[Control Agents for Other Pests]

In addition, the heteroaryl pyrimidine compounds of the present invention are excellent in the effect of controlling insect pests having a stinger or venom which harm humans and animals, insect pests that mediate various pathogens/pathogenic microbes, and insect pests that cause discomfort to humans (such as toxic pests, hygiene pests and unpleasant pests).

Specific examples thereof are shown below.

(1) Insect Pests of the Order Hymenoptera

Bees belonging to the family Argidae, bees belonging to the family Cynipidae, bees belonging to the family Diprionidae, ants belonging to the family Formicidae, bees belonging to the family Mutillidae, bees belonging to the family Vespidae.

(2) Other Pests

Cockroaches (Blattodea), termites, spiders (Araneae), centipedes, millipedes, crustaceans, bedbugs (*Cimex lectularius*).

EXAMPLES

[Pharmaceutical Formulation]

Although some pharmaceutical formulations of the pest control agent, insecticidal or acaricidal agent, ectoparasite control agent, or endoparasite control- or endoparasite-expelling agent of the present invention are shown, additives and the addition ratios should not be limited to these examples and can be modified over a wide range. The term "part" in the formulations indicates "part by weight".

The formulations for agricultural and horticultural use and for paddy rice are shown below.

(Formulation 1: Wettable Powder)

40 parts of the heteroaryl pyrimidine compound of the present invention, 53 parts of diatomaceous earth, 4 parts of a higher alcohol sulfuric acid ester and 3 parts of an alkyl naphthalene sulfonate are uniformly mixed and finely pulverized to obtain a wettable powder containing 40% of an active ingredient.

(Formulation 2: emulsion)

30 parts of the heteroaryl pyrimidine compound of the present invention, 33 parts of xylene, 30 parts of dimethylformamide and 7 parts of a polyoxyethylene alkyl allyl ether are mixed and dissolved to obtain an emulsion containing 30% of an active ingredient.

(Formulation 3: Granule)

5 parts of the heteroaryl pyrimidine compound of the present invention, 40 parts of talc, 38 parts of clay, 10 parts of bentonite and 7 parts of a sodium alkylsulfate are uniformly mixed and finely pulverized, and then granulated into a granular form having a diameter of 0.5 to 1.0 mm to obtain a granule containing 5% of an active ingredient.

(Formulation 4: granule)

5 parts of the heteroaryl pyrimidine compound of the present invention, 73 parts of clay, 20 parts of bentonite, 1 part of sodium dioctyl sulfosuccinate and 1 part of potassium phosphate are thoroughly ground and mixed, water is added and thoroughly kneaded, followed by granulation and drying to obtain a granule containing 5% of an active ingredient.

(Formulation 5: Suspension)

10 parts of the heteroaryl pyrimidine compound of the present invention, 4 parts of a polyoxyethylene alkyl allyl ether, 2 parts of a polycarboxylic acid sodium salt, 10 parts of glycerin, 0.2 parts of xanthan gum and 73.8 parts of water are mixed and subjected to wet grinding until the particle size becomes 3 microns or less to obtain a suspension containing 10% of an active ingredient.

The formulations of an ectoparasite control agent or an endoparasite control- or endoparasite-expelling agent are shown below.

(Formulation 6: granule)

5 parts of the heteroaryl pyrimidine compound of the present invention are dissolved in an organic solvent to obtain a solution, the solution is sprayed onto 94 parts of kaolin and 1 part of white carbon, and then the solvent is evaporated under reduced pressure. This type of granule can be mixed with animal feed.

(Formulation 7: injection)

0.1 to 1 part of the heteroaryl pyrimidine compound of the present invention and 99 to 99.9 parts of peanut oil are uniformly mixed and then sterilized by filtration through a sterilizing filter.

(Formulation 8: pour-on agent)

5 parts of the heteroaryl pyrimidine compound of the present invention, 10 parts of a myristic acid ester and 85 parts of isopropanol are uniformly mixed to obtain a pour-on agent.

(Formulation 9: Spot-on Agent)

10 to 15 parts of the heteroaryl pyrimidine compound of the present invention, 10 parts of a palmitic acid ester and 75 to 80 parts of isopropanol are uniformly mixed to obtain a spot-on agent.

(Formulation 10: spraying agent)

1 part of the heteroaryl pyrimidine compound of the present invention, 10 parts of propylene glycol and 89 parts of isopropanol are uniformly mixed to obtain a spraying agent.

Next, the present invention will be described in more detail by showing compound examples. However, the present invention is in no way limited by the following compound examples.

Example 1

5-(ethylsulfonyl)-4-(5-(2,2,2-trifluoroethoxy)pyridin-2-yl)-2,2'-bipyrimidine Synthesis of [5-(ethylsulfonyl)-4-(5-(2,2,2-trifluoroethoxy)pyridin-2-yl)-2,2'-bipyrimidine] (Compound No. 1-2)

(Step 1) Synthesis of 2-bromo-5-((triisopropylsilyl)oxy)pyridine [2-bromo-5-((triisopropylsilyl)oxy)pyridine]

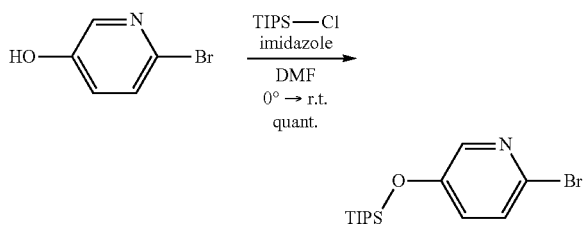

6-bromopyridin-3-ol (23 g) and imidazole (11 g) were dissolved in N,N-dimethylformamide (130 ml) and stirred at 0° C. Triisopropylsilyl chloride (34 ml, 0.90 g/ml) was added thereto, and the resulting mixture was stirred overnight at room temperature. The obtained liquid was poured into a saturated sodium hydrogen carbonate solution and extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 45 g (yield quantity) of a desired product.

$^1$H-NMR measurement results of the obtained desired product are shown below.

$^1$H-NMR (400 MHz, CDCl$_3$): δ 8.02 (d, 1H), 7.32 (d, 1H), 7.07 (dd, 1H), 1.29-1.20 (m, 3H), 1.10 (d, 18H).

(Step 2) 2-(ethylthio)-1-morpholinoethan-1-one

Synthesis of 2-(ethylthio)-1-morpholinoethan-1-one

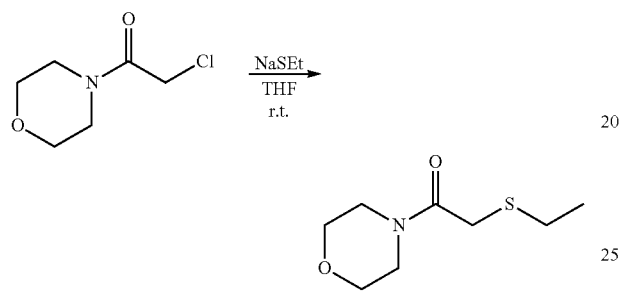

4-(chloroacetyl)morpholine (1 g) was dissolved in tetrahydrofuran (30 ml) and stirred at 0° C. Sodium ethyl mercaptan (0.64 g, 80%) was added thereto, and the resulting mixture was stirred overnight at room temperature. The obtained solution was diluted with diethyl ether and filtered through celite. The filtrate was concentrated under reduced pressure, and the obtained residue (1.3 g) was used in the next step without purification.

$^1$H-NMR measurement results of the obtained desired product are shown below.

$^1$H-NMR (400 MHz, CDCl3): δ 3.74-3.50 (m, 8H), 3.32 (s, 2H), 2.67 (q, 2H), 1.30 (t, 3H).

(Step 3) 2-(ethylthio)-1-(5-((triisopropylsilyl)oxy)pyridin-2-yl)ethan-1-one

Synthesis of [2-(ethylthio)-1-(5-((triisopropylsilyl)oxy)pyridin-2-yl)ethan-1-one]

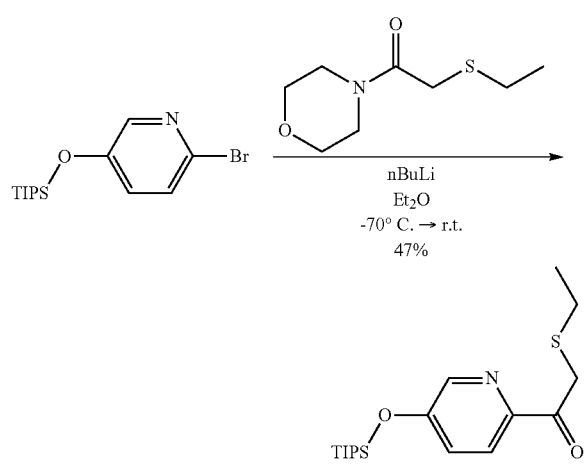

2-bromo-5-((triisopropylsilyl)oxy) pyridine (1.8 g) was dissolved in tetrahydrofuran (30 ml), and the reaction vessel was purged with nitrogen and then cooled to −70° C. n-butyllithium (2.65 M, n-hexane solution, 2.5 ml) was added dropwise thereto, and the resulting mixture was stirred at −70° C. for 1 hour. The 2-(ethylthio)-1-morpholinoethan-1-one (1.2 g) obtained in Step 2 was added thereto, and the resulting mixture was stirred at room temperature for 2 hours. The obtained liquid was poured into water and extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.90 g (yield: 47%) of a desired product.

$^1$H-NMR measurement results of the obtained desired product are shown below.

$^1$H-NMR (400 MHz, CDCl$_3$): δ 8.26 (d, 1H), 8.03 (d, 1H), 7.25 (dd, 1H), 4.03 (s, 2H), 2.62 (q, 2H), 1.36-1.22 (m, 6H), 1.11 (d, 18H).

(Step 4) 2-(ethylsulfonyl)-1-(5-((triisopropylsilyl)oxy)pyridin-2-yl)ethan-1-one Synthesis of [2-(ethylsulfonyl)-1-(5-((triisopropylsilyl)oxy)pyridin-2-yl)ethan-1-one]

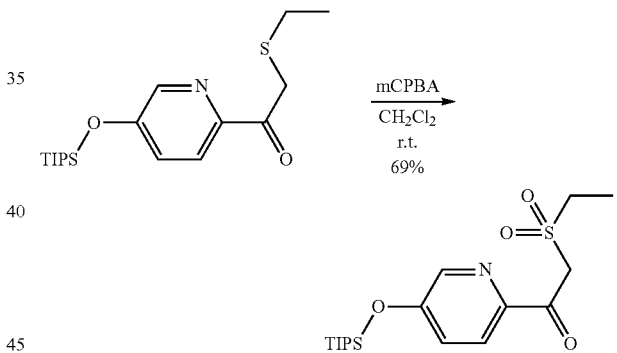

2-(ethylthio)-1-(5-((triisopropylsilyl)oxy)pyridin-2-yl)ethan-1-one (9.2 g) was dissolved in dichloromethane (260 ml) and stirred at 0° C. Meta-chloroperoxybenzoic acid (70%, 14 g) was added thereto, and the resulting mixture was stirred at room temperature for 1 hour. The obtained liquid was poured into a mixed solution of a saturated aqueous sodium bicarbonate solution and a saturated aqueous sodium thiosulfate solution, and extracted with dichloromethane. The obtained organic layer was washed with saturated brine, dried over anhydrous magnesium sulfate, and filtered. The filtrate was concentrated under reduced pressure, and the obtained residue was purified by silica gel column chromatography to obtain 6.9 g (yield: 69%) of a desired product.

$^1$H-NMR measurement results of the obtained desired product are shown below.

$^1$H-NMR (400 MHz, CDCl$_3$): δ 8.30 (d, 1H), 8.01 (d, 1H), 7.27 (dd, 1H), 4.95 (s, 2H), 3.31 (q, 2H), 1.46 (t, 3H), 1.36-1.24 (m, 3H), 1.12 (d, 18H).

(Step 5) 3-(dimethylamino)-2-(ethylsulfonyl)-1-(5-hydroxypyridin-2-yl)prop-2-en-1-one Synthesis of [3-(dimethylamino)-2-(ethylsulfonyl)-1-(5-hydroxypyridin-2-yl)prop-2-en-1-one]

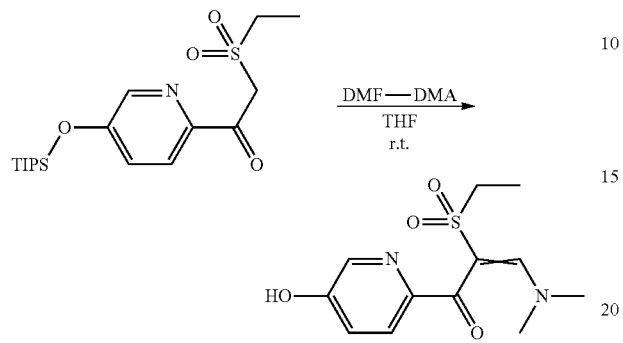

2-(ethylsulfonyl)-1-(5-((triisopropylsilyl)oxy)pyridin-2-yl)ethan-1-one (0.5 g) was dissolved in tetrahydrofuran (7 ml) and stirred at room temperature. N,N-dimethylformamide dimethyl acetal (0.23 g) was added thereto, and the resulting mixture was stirred at 50° C. for 1 hour. The obtained liquid was concentrated under reduced pressure, and the obtained residue was used in the next step without purification.

(Step 6) 6-(5-(ethylsulfonyl)-[2,2'-bipyrimidin]-4-yl)pyridin-3-ol

Synthesis of [6-(5-(ethylsulfonyl)-[2,2'-bipyrimidin]-4-yl)pyridin-3-ol]

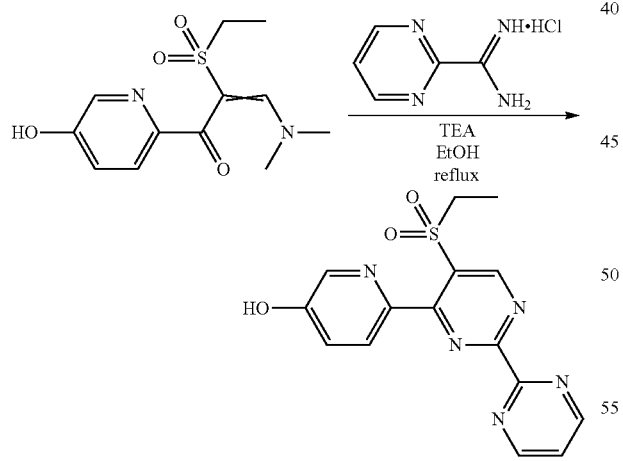

The 3-(dimethylamino)-2-(ethylsulfonyl)-1-(5-hydroxypyridin-2-yl)prop-2-en-1-one obtained in Step 5 was dissolved in ethanol (8 ml) and stirred at room temperature. Triethylamine (0.40 g) and 2-amidinopyrimidine hydrochloride (0.20 g) were added thereto, and the resulting mixture was stirred for 1 hour with heating under reflux. The obtained liquid was concentrated under reduced pressure, and the obtained residue was used in the next step without purification.

(Step 7) 5-(ethylsulfonyl)-4-(5-(2,2,2-trifluoroethoxy)pyridin-2-yl)-2,2'-bipyrimidine Synthesis of [5-(ethylsulfonyl)-4-(5-(2,2,2-trifluoroethoxy)pyridin-2-yl)-2,2'-bipyrimidine]

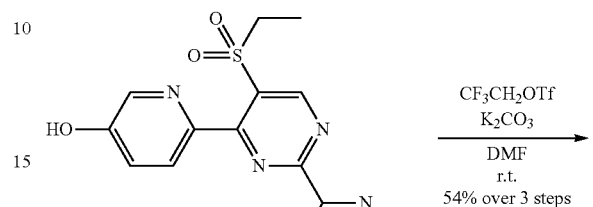

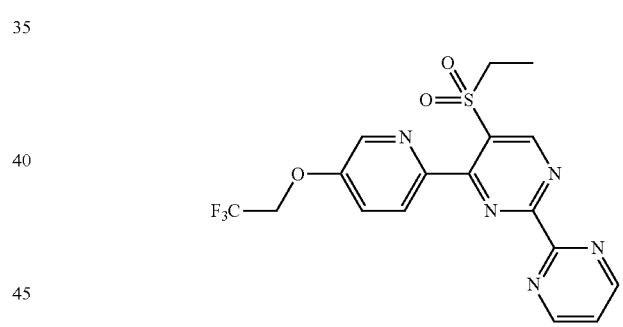

The 6-(5-(ethylsulfonyl)-[2,2'-bipyrimidin]-4-yl)pyridin-3-ol obtained in Step 6 was dissolved in N,N-dimethylformamide (13 ml) and stirred at room temperature. Potassium carbonate (0.54 g) and 2,2,2-trifluoroethyl triflate (0.91 g) were added thereto, and the resulting mixture was stirred overnight at room temperature. The obtained liquid was poured into water and extracted with ethyl acetate. The obtained organic layer was washed with saturated brine, dried over anhydrous magnesium sulfate, and filtered. The filtrate was concentrated under reduced pressure, and the obtained residue was purified by silica gel column chromatography to obtain 0.30 g (yield: 54%, 3 steps) of a desired product.

$^1$H-NMR measurement results of the obtained desired product are shown below.

$^1$H-NMR (400 MHz, CDCl$_3$): δ 9.62 (s, 1H), 9.09 (m, 2H), 8.44 (d, 1H), 8.24 (d, 1H), 7.52 (t, 1H), 7.46 (dd, 1H), 4.50 (q, 2H), 4.05 (q, 2H), 1.46 (t, 3H).

Example 2

5-(ethylsulfonyl)-4-(5-(nonafluorobutyl)pyridin-2-yl)-2,2'-bipyrimidine Synthesis of [5-(ethylsulfonyl)-4-(5-(nonafluorobutyl)pyridin-2-yl)-2,2'-bipyrimidine](Compound No. 2-3)

(Step 1) 2-(1-ethoxyvinyl)-5-(nonafluorobutyl)pyridine

Synthesis of [2-(1-ethoxyvinyl)-5-(nonafluorobutyl)pyridine]

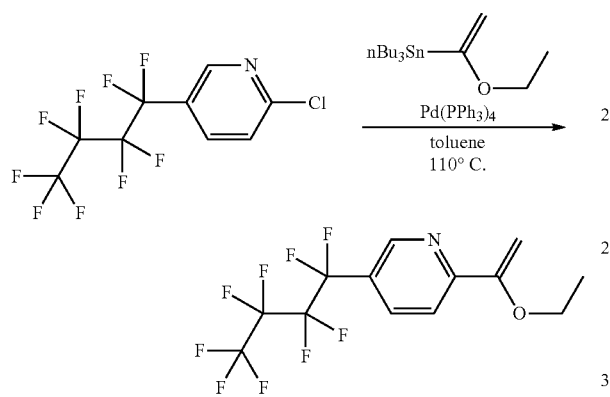

2-chloro-5-(nonafluorobutyl)pyridine (3.3 g) synthesized using the perfluoroalkylation reaction of an aromatic compound described in Japanese Unexamined Patent Application, First Publication No. 2015-86221 was dissolved in toluene (20 ml), and after purging the reaction system with argon, stirred at room temperature. Tributyl(1-ethoxyvinyl)tin (3.6 g) and tetrakis (triphenylphosphine) palladium (0) (0.58 g) were added thereto, and the resulting mixture was stirred at 110° C. for 22 hours. The obtained liquid was allowed to cool to room temperature and filtered through celite. The filtrate was concentrated under reduced pressure.

(Step 2) 2-bromo-1-(5-(nonafluorobutyl)pyridin-2-yl)ethan-1-one

Synthesis of [2-bromo-1-(5-(nonafluorobutyl)pyridin-2-yl)ethan-1-one]

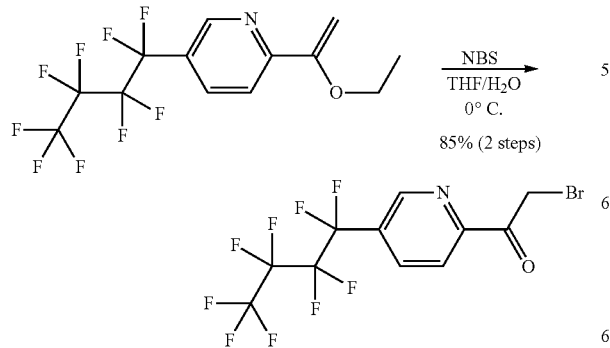

The concentrate (containing 2-(1-ethoxyvinyl)-5-(nonafluorobutyl)pyridine) obtained in Step 1 was dissolved in a mixed solvent of tetrahydrofuran (26 ml) and water (2.6 ml) and stirred at 0° C. N-bromosuccinimide (2.1 g) was added thereto, and the resulting mixture was stirred for 40 minutes. The obtained liquid was poured into water and extracted with ethyl acetate. The obtained organic layer was washed with saturated brine, dried over anhydrous magnesium sulfate, and filtered. The filtrate was concentrated under reduced pressure, and the obtained concentrate was purified by silica gel column chromatography to obtain 3.5 g (yield: 85%, 2 steps) of a desired product.

$^1$H-NMR measurement results of the obtained desired product are shown below.

$^1$H-NMR (400 MHz, CDCl$_3$): δ 8.89 (d, 1H), 8.22 (d, 1H), 8.09 (dd, 1H), 4.82 (s, 2H).

(Step 3) 2-(ethylthio)-1-(5-(nonafluorobutyl)pyridin-2-yl)ethan-1-one

Synthesis of [2-(ethylthio)-1-(5-(nonafluorobutyl)pyridin-2-yl)ethan-1-one]

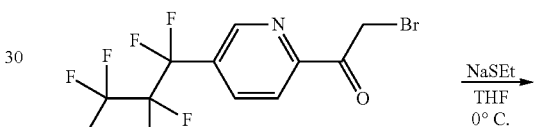

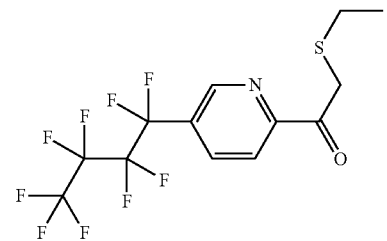

2-bromo-1-(5-(nonafluorobutyl)pyridin-2-yl)ethan-1-one (3.5 g) was dissolved in tetrahydrofuran (25 ml) and stirred at 0° C. Sodium ethyl mercaptan (90%, 0.86 g) was added thereto, and the resulting mixture was stirred for 45 minutes. The obtained liquid was poured into a saturated aqueous ammonium chloride solution and extracted with ethyl acetate. The obtained organic layer was washed with saturated brine, dried over anhydrous magnesium sulfate, and filtered. The filtrate was concentrated under reduced pressure.

(Step 4) 2-(ethylsulfonyl)-1-(5-(nonafluorobutyl)pyridin-2-yl)ethan-1-one

Synthesis of [2-(ethylsulfonyl)-1-(5-(nonafluorobutyl)pyridin-2-yl)ethan-1-one]

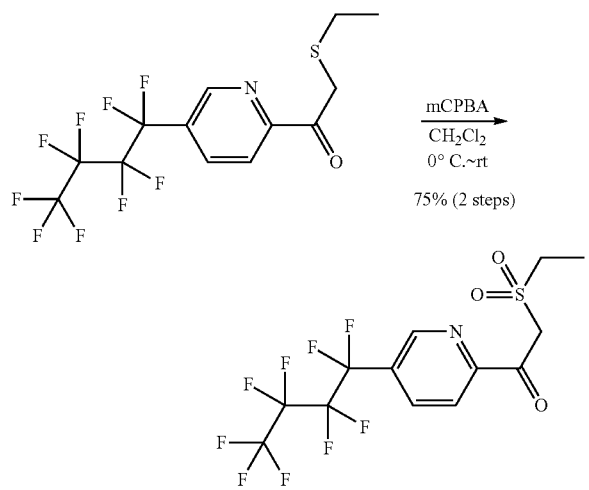

The concentrate (containing 2-(ethylthio)-1-(5-(nonafluorobutyl)pyridin-2-yl)ethan-1-one) obtained in Step 3 was dissolved in dichloromethane (43 ml) and stirred at 0° C. Meta-chloroperoxybenzoic acid (70%, 4.6 g) was added thereto, and the resulting mixture was stirred at room temperature overnight. The obtained liquid was poured into a mixed solution of a saturated aqueous sodium bicarbonate solution and a saturated aqueous sodium thiosulfate solution, and extracted with chloroform. The obtained organic layer was dried over anhydrous magnesium sulfate and filtered. The filtrate was concentrated under reduced pressure, and the obtained concentrate was purified by silica gel column chromatography to obtain 2.7 g (yield: 75%, 2 steps) of a desired product.

$^1$H-NMR measurement results of the obtained desired product are shown below.

$^1$H-NMR (400 MHz, CDCl$_3$): 8.95 (d, 1H), 8.24 (d, 1H), 8.11 (dd, 1H), 5.00 (s, 2H), 3.30 (q, 2H), 1.47 (t, 3H).

(Step 5) 3-(dimethylamino)-2-(ethylsulfonyl)-1-(5-nonafluorobutyl)pyridin-2-yl)prop-2-en-1-one Synthesis of [3-(dimethylamino)-2-(ethylsulfonyl)-1-(5-(nonafluorobutyl)pyridin-2-yl)prop-2-en-1-one]

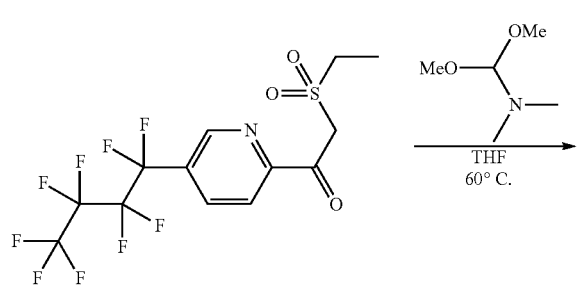

2-(ethylsulfonyl)-1-(5-(nonafluorobutyl)pyridin-2-yl)ethan-1-one (1.0 g) was dissolved in tetrahydrofuran (12 ml) and stirred at room temperature. N,N-dimethylformamide dimethyl acetal (1.4 g) was added thereto, and the resulting mixture was stirred at 60° C. for 100 minutes. The obtained liquid was concentrated under reduced pressure.

(Step 6) 5-(ethylsulfonyl)-4-(5-(nonafluorobutyl)pyridin-2-yl)-2,2'-bipyrimidine Synthesis of [5-(ethylsulfonyl)-4-(5-(nonafluorobutyl)pyridin-2-yl)-2,2'-bipyrimidine]

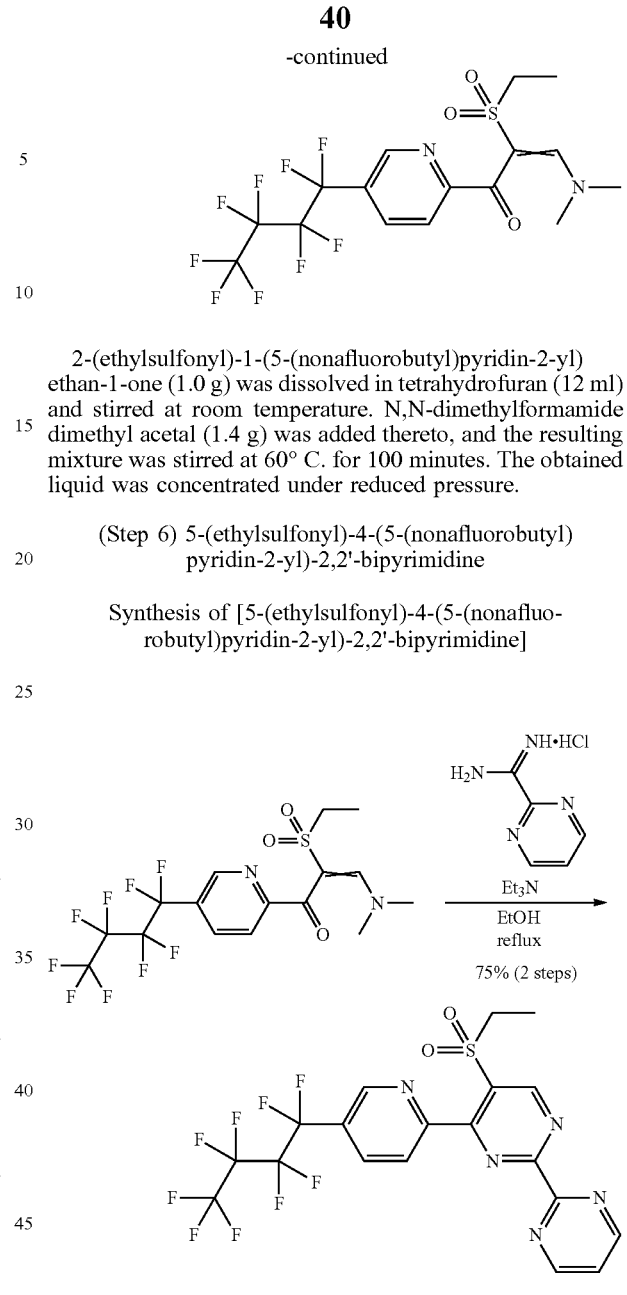

The concentrate (containing (3-(dimethylamino)-2-(ethylsulfonyl)-1-(5-nonafluorobutyl)pyridin-2-yl)prop-2-en-1-one) (0.20 g) obtained in Step 5 was dissolved in ethanol (2.1 ml) and stirred at room temperature. Triethylamine (0.19 g) and 2-amidinopyrimidine hydrochloride (0.098 g) were added thereto, and the resulting mixture was stirred for 2 hours with heating under reflux. The obtained liquid was poured into a saturated aqueous ammonium chloride solution and extracted with chloroform. The obtained organic layer was dried over anhydrous magnesium sulfate and filtered. The filtrate was concentrated under reduced pressure, and the obtained concentrate was purified by silica gel column chromatography to obtain 0.17 g (yield: 75%, 2 steps) of a desired product.

$^1$H-NMR measurement results of the obtained desired product are shown below.

$^1$H-NMR (400 MHz, CDCl$_3$): 9.65 (s, 1H), 9.08 (d, 2H), 8.89 (d, 1H), 8.25 (d, 1H), 8.15 (dd, 1H), 7.53 (t, 1H), 3.97 (q, 2H), 1.45 (t, 3H).

Examples of the heteroaryl pyrimidine compounds of the present invention produced by the same method as in the above Examples are shown in Tables 1 and 2. Table 1 shows substituents in the compound represented by the formula (I-1). Physical property data of the compounds were entered in the column of "Physical properties". As the physical property data, properties or melting points (m.p.) were described. In the tables, Me represents a methyl group, Et represents an ethyl group, iPr represents an isopropyl group, cPr represents a cyclopropyl group, tBu represents a tertiary butyl group, Ac represents an acetyl group, and Ts represents a paratoluenesulfonyl group.

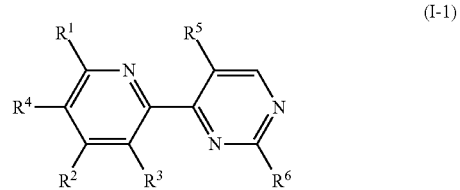

(I-1)

TABLE 1

| Compound No. | $R^1$ | $R^2$ | $R^3$ | $R^4$ | $R^5$ | $R^6$ | Physical properties |
|---|---|---|---|---|---|---|---|
| 1-1 | H | H | H | OCH$_2$CF$_2$CF$_3$ | SO$_2$Et | pyrimidin-2-yl | m.p.: 119-121 (° C.) |
| 1-2 | H | H | H | OCH$_2$CF$_3$ | SO$_2$Et | pyrimidin-2-yl | m.p.: 165-167 (° C.) |
| 1-3 | H | H | H | OCH$_2$CF$_2$CF$_2$CF$_3$ | SO$_2$Et | pyrimidin-2-yl | m.p.: 124-126 (° C.) |
| 1-4 | H | H | H | OCH$_2$CF$_2$CF$_3$ | SO$_2$Et | 5-F-pyrimidin-2-yl | m.p.: 145-147 (° C.) |
| 1-5 | H | H | H | OCH$_2$CF$_2$CF$_3$ | SO$_2$Et | phenyl | m.p.: 120-122 (° C.) |
| 1-6 | H | H | H | OCH$_2$CF$_2$CF$_3$ | SO$_2$Et | 4-F-phenyl | m.p.: 149-151 (° C.) |
| 1-7 | H | H | H | OCH$_2$CF$_2$CF$_3$ | SO$_2$Et | pyridin-2-yl | m.p.: 145-147 (° C.) |
| 1-8 | H | H | H | OCH$_2$CF$_2$CF$_3$ | SO$_2$Et | pyridin-4-yl | m.p.: 146-148 (° C.) |
| 1-9 | H | H | H | OCH$_2$CF$_2$CF$_3$ | SO$_2$Et | pyridin-3-yl | m.p.: 137-139 (° C.) |
| 1-10 | H | H | H | OCH$_2$CF$_2$CHFCF$_3$ | SO$_2$Et | pyrimidin-2-yl | $n_D$ (23.5° C.) 1.153 |
| 1-11 | H | H | H | OCH$_2$CF$_2$CHF$_2$ | SO$_2$Et | pyrimidin-2-yl | viscous oil |
| 1-12 | H | H | H | OCH$_2$CF$_2$CF$_2$CF$_2$CHF$_2$ | SO$_2$Et | pyridin-2-yl | m.p.: 88-91 (° C.) |
| 1-13 | H | H | H | OCH$_2$CF$_2$CF$_3$ | SO$_2$Et | 2-F-phenyl | m.p.: 99-101 (° C.) |
| 1-14 | H | H | H | OCH$_2$CF$_2$CF$_3$ | SO$_2$Et | 3-F-phenyl | m.p.: 130-131 (° C.) |
| 1-15 | H | H | H | OCH$_2$CF$_2$CF$_3$ | SO$_2$Et | 1-(CH$_2$OCH$_2$CH$_2$SiMe$_3$)-1H-1,2,4-triazol-3-yl | m.p.: 115-117 (° C.) |
| 1-16 | H | H | H | OCH$_2$CF$_2$CF$_3$ | SO$_2$Et | 1-Me-1H-1,2,4-triazol-5-yl | m.p.: 126-128 (° C.) |
| 1-17 | H | H | H | OCH$_2$CF$_2$CF$_3$ | SO$_2$Et | 1-(CHF$_2$)-1H-1,2,4-triazol-3-yl | m.p.: 87-89 (° C.) |
| 1-18 | H | H | H | OCH$_2$CF$_2$CF$_3$ | SO$_2$Et | 1-Ac-1H-1,2,4-triazol-3-yl | m.p.: 66-69 (° C.) |
| 1-19 | H | H | H | OCH$_2$CF$_2$CF$_2$CF$_3$ | SO$_2$Et | 1H-1,2,4-triazol-3-yl | m.p.: 138-140 (° C.) |
| 1-20 | H | H | H | OCH$_2$CF$_2$CF$_2$CF$_3$ | SO$_2$Et | 1-(CHF$_2$)-1H-1,2,4-triazol-3-yl | m.p.: 72-75 (° C.) |
| 1-21 | H | H | H | OCH$_2$CF$_2$CF$_2$CF$_3$ | SO$_2$Et | 1-Me-1H-1,2,4-triazol-5-yl | m.p.: 94-97 (° C.) |
| 1-22 | H | H | H | OCH$_2$CF$_2$CF$_3$ | SO$_2$Et | 1-Et-1H-1,2,4-triazol-5-yl | m.p.: 96-99 (° C.) |
| 1-23 | H | H | H | OCH$_2$CF$_2$CF$_3$ | SO$_2$Et | 1-Me-1H-1,2,4-triazol-3-yl | m.p.: 213-216 (° C.) |
| 1-24 | H | H | H | OCH$_2$CF$_2$CF$_2$CF$_3$ | SO$_2$Et | 1-(CH$_2$CF$_3$)-1H-1,2,4-triazol-5-yl | m.p.: 141-143 (° C.) |
| 1-25 | H | H | H | OCH$_2$CH$_2$CH$_2$CH$_3$ | SO$_2$Et | 1-Me-1H-1,2,4-triazol-3-yl | m.p.: 75-78 (° C.) |
| 1-26 | H | H | H | OCH$_2$CH$_2$CH$_3$ | SO$_2$Et | 1-Me-1H-1,2,4-triazol-3-yl | m.p.: 69-72 (° C.) |
| 1-27 | H | H | H | OCH$_2$CF$_2$CF$_2$CF$_3$ | SO$_2$Et | 1-Me-1H-1,2,4-triazol-3-yl | m.p.: 162-163 (° C.) |
| 1-28 | H | H | H | 4-I-1H-pyrazol-1-yl | SO$_2$Et | pyridin-2-yl | m.p: 253-255 (° C.) |
| 1-29 | H | H | H | OCH$_2$CF$_2$CF$_2$CF$_3$ | SO$_2$Et | 1-(CH$_2$OCH$_2$CH$_2$SiMe$_3$)-1H-1,2,4-triazol-3-yl | amorphous |
| 1-30 | H | H | H | OCH$_2$CF$_2$CF$_2$CF$_3$ | SO$_2$Et | NH$_2$ | m.p.: 163-165 (° C.) |
| 1-31 | H | H | H | 4-(CF$_2$CF$_3$)-1H-pyrazol-1-yl | SO$_2$Et | pyridin-2-yl | m.p.: 145-149 (° C.) |
| 1-32 | H | H | H | OCH$_2$CF$_2$CF$_3$ | SO$_2$Et | NH$_2$ | m.p.: 163-165 (° C.) |
| 1-33 | H | H | H | OCH$_2$CF$_2$CF$_3$ | SO$_2$Et | 1H-1,2,4-triazol-3-yl | m.p.: 136-138 (° C.) |
| 1-34 | H | H | H | 4-(CH=CH$_2$)-1H-pyrazol-1-yl | SO$_2$Et | pyridin-2-yl | m.p.: 206-211 (° C.) |
| 1-35 | H | H | H | OCH$_2$CF$_2$CF$_2$CF$_3$ | SO$_2$Et | Me | m.p.: 84-86 (° C.) |
| 1-36 | H | H | H | CH=CCl$_2$ | SO$_2$Et | pyridin-2-yl | m.p.: 198-199 (° C.) |
| 1-37 | H | H | H | OCH$_2$CF$_2$CF$_3$ | SO$_2$Et | 1-(CH$_2$cPr)-1H-1,2,4-triazol-5-yl | m.p.: 103-105 (° C.) |
| 1-38 | H | H | H | OCH$_2$CF$_2$CF$_3$ | SO$_2$Et | 1-(CH$_2$cPr)-1H-1,2,4-triazol-3-yl | viscous oil |
| 1-39 | H | H | H | SEt | SEt | 1-Me-1H-1,2,4-triazol-3-yl | m.p.: 163-165 (° C.) |
| 1-40 | H | H | H | OCH$_2$CF$_2$CF$_3$ | SEt | 1-Me-1H-1,2,4-triazol-3-yl | m.p.: 139-141 (° C.) |
| 1-41 | H | H | H | OCH$_2$CF$_2$CF$_3$ | SOEt | 1-Me-1H-1,2,4-triazol-3-yl | m.p.: 133-136 (° C.) |
| 1-42 | H | H | H | SO$_2$Et | SO$_2$Et | 1-Me-1H-1,2,4-triazol-3-yl | amorphous |
| 1-43 | H | H | H | OCH$_2$CF$_2$CF$_2$CF$_3$ | SO$_2$Et | Et | m.p.: 89-91 (° C.) |
| 1-44 | H | H | H | benzyloxy | SO$_2$Et | NH$_2$ | m.p.: 177-182 (° C.) |
| 1-45 | H | H | H | OCH$_2$CF$_2$CF$_3$ | SO$_2$Et | 5-NH$_2$-1H-1,2,4-triazol-1-yl | m.p.: 210-215 (° C.) |
| 1-46 | H | H | H | OCH$_2$CF$_2$CF$_3$ | SO$_2$Et | 3-NH$_2$-1H-1,2,4-triazol-1-yl | m.p.: 240-244 (° C.) |
| 1-47 | H | H | H | CH=NOCH$_2$CF$_3$ | SO$_2$Et | pyridin-2-yl | m.p.: 143-145 (° C.) |
| 1-48 | H | H | H | OCH$_2$CF$_2$CF$_2$CF$_3$ | SO$_2$Et | OMe | m.p.: 116-118 (° C.) |
| 1-49 | H | H | H | OCH$_2$CF$_2$CF$_2$CF$_3$ | SO$_2$Et | 3-NH$_2$-1H-1,2,4-triazol-1-yl | m.p.: 255-257 (° C.) |
| 1-50 | H | H | H | OCH$_2$CF$_2$CF$_2$CF$_3$ | SO$_2$Et | 5-NH$_2$-1H-1,2,4-triazol-1-yl | m.p.: 255-257 (° C.) |
| 1-51 | H | H | H | benzyloxy | SO$_2$Et | pyridin-2-yl | m.p.: 156-158 (° C.) |
| 1-52 | H | H | H | OSO$_2$CF$_3$ | SO$_2$Et | pyridin-2-yl | m.p.: 154-156 (° C.) |
| 1-53 | H | H | H | OCH$_2$CF$_2$CHFCF$_3$ | SO$_2$Et | OMe | m.p.: 145-147 (° C.) |
| 1-54 | H | H | H | OCH$_2$CF$_2$CHFCF$_3$ | SO$_2$Et | NH$_2$ | m.p.: 161-163 (° C.) |
| 1-55 | H | H | H | OCH$_2$CF$_2$CHFCF$_3$ | SO$_2$Et | 3-NH$_2$-1H-1,2,4-triazol-1-yl | m.p.: 242-244 (° C.) |

TABLE 1-continued

| Compound No. | R¹ | R² | R³ | R⁴ | R⁵ | R⁶ | Physical properties |
|---|---|---|---|---|---|---|---|
| 1-56 | H | H | H | OCH$_2$CF$_2$CHFCF$_3$ | SO$_2$Et | 5-NH$_2$-1H-1,2,4-triazol-1-yl | m.p.: 242-244 (° C.) |
| 1-57 | H | H | H | OCH$_2$CF$_2$CF$_2$CHF$_2$ | SO$_2$Et | OMe | m.p.: 109-111 (° C.) |
| 1-58 | H | H | H | OCH$_2$CF$_2$CF$_2$CHF$_2$ | SO$_2$Et | NH$_2$ | m.p.: 148-150 (° C.) |
| 1-59 | H | H | H | OCH$_2$CF$_2$CHF$_2$ | SO$_2$Et | OMe | m.p.: 144-146 (° C.) |
| 1-60 | H | H | H | OCH$_2$CF$_2$CHF$_2$ | SO$_2$Et | NH$_2$ | m.p.: 154-156 (° C.) |
| 1-61 | H | H | H | OCH$_2$CF$_2$CF$_2$CF$_3$ | SO$_2$Et | NHAc | m.p.: 151-153 (° C.) |
| 1-62 | H | H | H | OCH$_2$CF$_2$CF$_2$CF$_3$ | SO$_2$Et | NMe$_2$ | m.p.: 141-144 (° C.) |
| 1-63 | H | H | H | OCH$_2$CF$_2$CF$_2$CF$_3$ | SO$_2$Et | Cl | m.p.: 127-128 (° C.) |
| 1-64 | H | H | H | OCH$_2$CF$_2$CF$_2$CF$_3$ | SO$_2$Et | NMeNH$_2$ | m.p.: 120-123 (° C.) |
| 1-65 | H | H | H | OCH$_2$CF$_2$CF$_2$CF$_3$ | SO$_2$Et | NHNH$_2$ | m.p.: 177-179 (° C.) |
| 1-66 | H | H | H | OCH$_2$CF$_2$CF$_2$CF$_3$ | SO$_2$Et | NHCONHMe | m.p.: 96-100 (° C.) |
| 1-67 | H | H | H | OCH$_2$CF$_2$CF$_2$CF$_3$ | SO$_2$Et | NHCO$^c$Pr | m.p.: 151-153 (° C.) |
| 1-68 | H | H | H | OCH$_2$CF$_2$CF$_2$CF$_3$ | SO$_2$Et | OCH$_2$$^c$Pr | n$_D$ (20.7° C.) 1.504 |
| 1-69 | H | H | H | OCH$_2$CF$_2$CF$_2$CF$_3$ | SO$_2$Et | ON | m.p.: 122-123 (° C.) |
| 1-70 | H | H | H | OCH$_2$CF$_2$CF$_2$CF$_3$ | SO$_2$Et | OCH$_2$CF$_3$ | m.p.: 139-141 (° C.) |
| 1-71 | H | H | H | OCH$_2$CF$_2$CF$_2$CF$_3$ | SO$_2$Et | NHCOO$^t$Bu | m.p.: 169-171 (° C.) |
| 1-72 | H | H | H | OCH$_2$CF$_2$CF$_2$CF$_3$ | SO$_2$Et | NHSO$_2$NMe$_2$ | m.p.: 186-188 (° C.) |
| 1-73 | H | H | H | OCH$_2$CF$_2$CF$_2$CF$_3$ | SO$_2$Et | NHNHTs | viscous oil |
| 1-74 | H | H | H | CF$_2$CF$_2$CF$_2$CF$_3$ | SO$_2$Et | NHAc | m.p.: 182-184 (° C.) |
| 1-75 | H | H | H | OCH$_2$CF$_2$CF$_2$CF$_3$ | SO$_2$Et | NHMe | m.p.: 144-147 (° C.) |
| 1-76 | H | H | H | OCH$_2$CF$_2$CF$_2$CF$_3$ | SO$_2$Et | CONH$_2$ | viscous oil |
| 1-77 | H | H | H | OCH$_2$CF$_2$CF$_2$CF$_3$ | SO$_2$Et | NHSO$_2$CF$_3$ | m.p.: 294-295 (° C.) |
| 1-78 | H | H | H | OCH$_2$CF$_2$CF$_2$CF$_3$ | SO$_2$Et | NHCOCH$_2$CH$_3$ | m.p.: 167-168 (° C.) |
| 1-79 | H | H | H | OCH$_2$CF$_2$CF$_2$CF$_3$ | SO$_2$Et | NHCO$^i$Pr | m.p.: 183-184 (° C.) |
| 1-80 | H | H | H | OCH$_2$CF$_2$CF$_2$CF$_3$ | SO$_2$Et | NHCOCF$_3$ | m.p.: 157-158 (° C.) |
| 1-81 | H | H | H | CF$_2$CF$_2$CF$_2$CF$_3$ | SO$_2$Et | 3-NH$_2$-1H-1,2,4-triazol-1-yl | m.p.: 280-282 (° C.) |
| 1-82 | H | H | H | CF$_2$CF$_2$CF$_2$CF$_3$ | SO$_2$Et | 5-NH$_2$-1H-1,2,4-triazol-1-yl | m.p.: 222-224 (° C.) |

TABLE 2

| Compound No. | Structural formula | Physical properties |
|---|---|---|
| 2-1 | (structure) | m.p.: 222-224 (° C.) |
| 2-2 | (structure) | m.p.: 171-173 (° C.) |
| 2-3 | (structure) | m.p.: 132-134 (° C.) |

TABLE 2-continued

| Compound No. | Structural formula | Physical properties |
| --- | --- | --- |
| 2-4 | | m.p.: 111-113 (° C.) |
| 2-5 | | m.p.: 115-117 (° C.) |
| 2-6 | | m.p.: 216-217 (° C.) |
| 2-7 | | m.p.: 177-179 (° C.) |
| 2-8 | | m.p.: 209-210 (° C.) |

TABLE 2-continued

| Compound No. | Structural formula | Physical properties |
|---|---|---|
| 2-9 | | m.p.: 191-192 (° C.) |
| 2-10 | | m.p.: 95-97 (° C.) |
| 2-11 | | m.p.: 212-214 (° C.) |
| 2-12 | (HBr salt) | m.p.: 234-239 (° C.) |
| 2-13 | | m.p.: 138-140 (° C.) |

TABLE 2-continued

| Compound No. | Structural formula | Physical properties |
|---|---|---|
| 2-14 | | m.p.: 174-176 (° C.) |
| 2-15 | | m.p.: 170-173 (° C.) |
| 2-16 | | m.p.: 182-185 (° C.) |
| 2-17 | | m.p.: 186-188 (° C.) |

Among the compounds shown in Tables 1 and 2, $^1$H-NMR data are shown below for compounds having physical properties of viscous oil or amorphous.

Compound No. (1-11): $^1$H-NMR (400 MHz, CDCl$_3$): δ 9.59 (s, 1H), 9.06 (d, 2H), 8.41 (d, 1H), 8.22 (d, 1H), 7.50 (t, 1H), 7.43 (dd, 1H), 5.17 (m, 1H), 4.47 (m, 1H), 4.01 (q, 2H), 1.43 (t, 3H).

Compound No. (1-29): $^1$H-NMR (400 MHz, CDCl$_3$) δ: 9.52 (1H, s), 8.47 (1H, s), 8.43 (1H, d, J=3.2 Hz), 8.26 (1H, d, J=9.1 Hz), 7.45 (1H, dd, J=8.8, 2.9 Hz), 5.68 (2H, s), 4.60 (2H, t, J=12.5 Hz), 4.04 (2H, q, J=7.4 Hz), 3.71 (2H, t, J=8.4 Hz), 1.45 (3H, t, J=7.5 Hz), 0.96 (2H, t, J=8.4 Hz), −0.01 (9H, s).

Compound No. (1-38): $^1$H-NMR (400 MHz, CDCl$_3$): δ 9.51 (s, 1H), 8.42 (d, 1H), 8.39 (s, 1H), 8.26 (d, 1H), 7.44 (dd, 1H), 4.57 (t, 2H), 4.21 (d, 2H), 4.03 (q, 2H), 1.50-1.41 (m, 4H), 0.80-0.75 (m, 2H), 0.51-0.47 (m, 2H).

Compound No. (1-42): $^1$H-NMR (400 MHz, CDCl$_3$): δ 9.55 (s, 1H), 9.14 (d, 1H), 8.41 (dd, 1H), 8.30 (d, 1H), 8.28 (s, 1H), 4.12 (s, 3H), 3.94 (q, 2H), 3.22 (q, 2H), 1.46 (t, 3H), 1.37 (t, 3H).

Compound No. (1-73): $^1$H-NMR (400 MHz, DMSO-d6, 140° C.): δ 9.89 (s, 1H), 9.45 (s, 1H), 8.64 (s, 1H), 8.44 (d, 1H), 7.78 (d, 1H), 7.68 (dd, 1H), 7.63 (d, 2H), 7.09 (d, 2H), 4.99 (t, 2H), 3.70 (q, 2H), 2.24 (s, 3H), 1.21 (t, 3H).

Compound No. (1-76): $^1$H-NMR (400 MHz, CDCl$_3$): δ 9.50 (s, 1H), 8.46 (d, 1H), 8.24 (d, 1H), 7.88 (brs, 1H), 7.50 (dd, 1H), 6.94 (drs, 1H), 4.65 (t, 2H), 4.06 (q, 2H), 1.45 (t, 3H).

[Biological Test]

The following test examples show that the heteroaryl pyrimidine compounds of the present invention are useful as an active ingredient of a pest control agent and an ectoparasite control agent. "Parts" are on a weight basis.

(Preparation of Test Emulsion)

5 parts of the heteroaryl pyrimidine compound of the present invention, 93.6 parts of dimethylformamide and 1.4 parts of a polyoxyethylene alkyl aryl ether were mixed and dissolved to prepare an emulsion (I) containing 5% of an active ingredient.

As a control, 98.5 parts of dimethylformamide and 1.5 parts of a polyoxyethylene alkyl aryl ether were mixed and dissolved to prepare an emulsion (II).

The insecticidal rate was calculated by the following formula.

Insecticidal rate (%)=(number of dead insects/number of tested insects)×100

(Test Example 1) Efficacy Test Against *Mythimna Separate*

0.8 g of a commercially available artificial diet (Insecta LFS, manufactured by Nosan Corporation) and 1 μl of the emulsion (1) were thoroughly mixed to obtain a test diet.

A plastic test container (1.4 ml volume) was filled with 0.2 g of test diet for each treatment group. Next, two second instar larvae of *Mythimna separata* were inoculated for each treatment group. A plastic lid was placed on the test container so that the second instar larvae of *Mythimna separata* would not escape. It was placed in a thermostatic chamber at 25° C., and the insecticidal rate and food intake were examined on the fifth day. The test was repeated twice.

The insecticidal rate and food intake were examined in the same manner as in Test Example 1 except that the emulsion (I) was changed to the emulsion (II) as a control.

The compounds with compound numbers shown in Table 3 were tested for efficacy against *Mythimna separata*. All the compounds showed an insecticidal rate against *Mythimna separata* of 100% or a food intake of 10% or less, relative to the control group. It can be seen that the heteroaryl pyrimidine compounds of the present invention are effective against *Mythimna separata*.

TABLE 3

| |
|---|
| 1-1 |
| 1-3 |
| 1-4 |
| 1-6 |
| 1-7 |
| 1-8 |
| 1-12 |
| 1-13 |
| 1-16 |
| 1-18 |
| 1-19 |
| 1-20 |
| 1-21 |
| 1-24 |
| 1-25 |
| 1-27 |
| 1-30 |
| 1-32 |
| 1-35 |
| 1-43 |
| 1-44 |
| 1-45 |
| 1-47 |
| 1-48 |
| 1-49 |
| 1-50 |
| 1-54 |
| 1-58 |
| 1-61 |
| 1-62 |
| 1-64 |

TABLE 3-continued

| |
|---|
| 1-65 |
| 1-66 |
| 1-67 |
| 1-68 |
| 1-78 |
| 1-79 |
| 1-80 |
| 2-1 |
| 2-2 |
| 2-3 |
| 2-4 |
| 2-5 |
| 2-7 |
| 2-9 |
| 2-10 |
| 2-13 |
| 2-14 |
| 2-15 |

(Test Example 2) Efficacy Test Against *Aphis craccivora*

Cowpea plants were raised in No. 3 pots, and nymphs of *Aphis craccivora* were inoculated on the primary leaves. The emulsion (1) was diluted with water so that the concentration of the compound of the present invention was 125 ppm, and the diluent was sprayed on the cowpea plants infested with nymphs of *Aphis craccivora*. The cowpea plants were placed in a thermostatic chamber with a temperature of 25° C. and a humidity of 60%. Viability of *Aphis craccivora* was evaluated when 4 days had passed since the spraying, and the insecticidal rate was calculated. The test was repeated twice.

The compounds with compound numbers shown in Table 4 were tested for efficacy against *Aphis craccivora*. All the compounds showed an insecticidal rate of 80% or more against *Aphis craccivora*.

TABLE 4

| |
|---|
| 1-1 |
| 1-2 |
| 1-9 |
| 1-11 |
| 1-15 |
| 1-21 |
| 1-25 |
| 1-29 |
| 1-32 |
| 1-33 |
| 1-35 |
| 1-61 |
| 1-62 |
| 1-65 |
| 1-78 |
| 1-80 |
| 2-2 |
| 2-3 |
| 2-4 |
| 2-5 |
| 2-6 |
| 2-9 |
| 2-10 |

(Test Example 3) Efficacy Test Against *Plutella xylostella*

The emulsion (1) was diluted with water so that the concentration of the compound of the present invention was 125 ppm. A cabbage leaf was immersed in the diluent for 30 seconds. This cabbage leaf was placed in a petri dish. Five second instar larvae of *Plutella xylostella* were released therein. The petri dish was placed in a thermostatic chamber with a temperature of 25° C. and a humidity of 60%. Viability was evaluated when 3 days had passed since the insect release, and the insecticidal rate was calculated. The test was repeated twice.

The compounds with compound numbers shown in Table 5 were tested for efficacy against *Plutella xylostella*. All the compounds showed an insecticidal rate of 80% or more against *Plutella xylostella*.

TABLE 5

| |
|---|
| 1-1 |
| 1-3 |
| 1-4 |
| 1-7 |
| 1-8 |
| 1-12 |
| 1-13 |
| 1-16 |
| 1-17 |
| 1-20 |
| 1-21 |
| 1-22 |
| 1-24 |
| 1-27 |
| 1-30 |
| 1-35 |
| 1-37 |
| 1-43 |
| 1-45 |
| 1-48 |
| 1-50 |
| 1-58 |
| 1-61 |
| 1-62 |
| 1-66 |
| 1-67 |
| 1-68 |
| 1-69 |
| 1-71 |
| 1-74 |
| 1-75 |
| 1-78 |
| 1-79 |
| 1-80 |
| 1-81 |
| 1-82 |
| 2-1 |
| 2-2 |
| 2-3 |
| 2-5 |
| 2-13 |

(Test Example 4) Efficacy Test Against *Phyllotreta striolata*

The emulsion (1) was diluted with water so that the concentration of the compound of the present invention was 125 ppm to prepare a test chemical. The test chemical was sprayed on bok choy seedlings (seventh true leaf development stage) planted in a No. 3 pot. The bok choy seedlings were air dried and then placed in a plastic cup. 10 adults of *Phyllotreta striolata* were released therein. The plastic cup was stored in a thermostatic chamber with a temperature of 25° C. and a humidity of 65%, viability was evaluated 7 days after the insect release, and the insecticidal rate was calculated. The test was repeated twice.

The compounds with compound numbers shown in Table 6 were tested for efficacy against adults of *Phyllotreta striolata*. All the compounds showed an insecticidal rate of 80% or more against adults of *Phyllotreta striolata*.

TABLE 6

| |
|---|
| 1-1 |
| 1-3 |
| 1-16 |
| 1-20 |
| 1-21 |
| 1-22 |
| 1-27 |
| 1-30 |
| 1-45 |
| 1-49 |
| 1-50 |
| 1-54 |
| 1-61 |
| 1-67 |
| 2-1 |
| 2-2 |
| 2-3 |

(Test Example 5) Efficacy Test Against *Nilaparvata lugens*

The emulsion (1) was diluted with water so that the concentration of the compound of the present invention was 125 ppm. Rice seedlings were immersed in the diluent for 30 seconds. The rice seedlings were air dried and then placed in a plastic case. Five second instar larvae of *Nilaparvata lugens* were released therein. The plastic case was stored in a thermostatic chamber with a temperature of 25° C. and a humidity of 65%, viability was evaluated 7 days after the inoculation, and the insecticidal rate was calculated. The test was repeated twice.

The compounds with compound numbers shown in Table 7 were tested for efficacy against *Nilaparvata lugens*. All the compounds showed an insecticidal rate of 80% or more against *Nilaparvata lugens*.

TABLE 7

| |
|---|
| 1-1 |
| 1-2 |
| 1-3 |
| 1-7 |
| 1-11 |
| 1-16 |
| 1-17 |
| 1-21 |
| 1-22 |
| 1-23 |
| 1-27 |
| 1-35 |
| 1-37 |
| 1-41 |
| 1-45 |
| 1-46 |
| 1-48 |
| 1-50 |
| 1-61 |
| 2-2 |
| 2-3 |
| 2-4 |
| 2-5 |
| 2-6 |
| 2-7 |
| 2-9 |

Since all of those randomly selected from among the heteroaryl pyrimidine compounds of the present invention exert the above-mentioned effects, it can be understood that the heteroaryl pyrimidine compounds of the present invention including the compounds that are not shown in examples are compounds having the effects of pest control, and in particular, acaricidal and insecticidal effects and the like. In addition, it can be understood that they are compounds also having an effect on parasites such as ectoparasites which are harmful to humans and animals.

INDUSTRIAL APPLICABILITY

The heteroaryl pyrimidine compound of the present invention can control pests which are problematic in terms of agricultural crops and hygiene. In particular, agricultural pests and mites and ticks can be effectively controlled at lower concentrations. Furthermore, it is possible to effectively control ectoparasites and endoparasites which harm humans and animals.

The invention claimed is:

1. A compound represented by a formula (I) or a salt thereof:

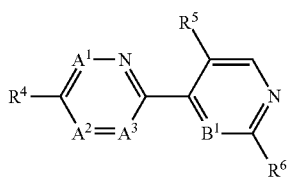

wherein
$A^1$ represents $CR'$ or a nitrogen atom;
$A^2$ represents $CR^2$ or a nitrogen atom;
$A^3$ represents $CR^3$ or a nitrogen atom;
provided that two or more of $A^1$ to $A^3$ do not represent nitrogen atoms at the same time;
$R'$, $R^2$ and $R^3$ each independently represent a hydrogen atom, a substituted or unsubstituted $C_{1-6}$ alkyl group, a hydroxyl group, a substituted or unsubstituted $C_{1-6}$ alkoxy group, a nitro group, a cyano group, a substituted or unsubstituted amino group or a halogeno group;
$B^1$ represents a nitrogen atom;
$R^4$ represents a substituted or unsubstituted $C_{1-6}$ alkyl group, a substituted or unsubstituted $C_{2-6}$ alkenyl group, a substituted or unsubstituted $C_{2-6}$ alkynyl group, a hydroxyl group, a substituted or unsubstituted $C_{1-6}$ alkoxy group, a formyl group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkylsulfonyloxy group, a substituted or unsubstituted $C_{3-8}$ cycloalkyl group, a substituted or unsubstituted 5- to 6-membered heteroaryl group, a substituted or unsubstituted amino group, a substituted or unsubstituted aminocarbonyl group, or a group represented by $—N=CR^aR^b$, wherein $R^a$ represents a hydrogen atom or a $C_{1-6}$ alkyl group, and $R^b$ represents a $C_{1-6}$ alkyl group;
$R^5$ represents a substituted or unsubstituted $C_{1-6}$ alkylthio group, a substituted or unsubstituted $C_{1-6}$ alkylsulfinyl group, or a substituted or unsubstituted $C_{1-6}$ alkylsulfonyl group;
$R^6$ represents a substituted or unsubstituted 5- to 6-membered heteroaryl group, a substituted or unsubstituted amino group of $—NR^gR^h$, or a substituted or unsubstituted aminocarbonyl group,
wherein $R^g$ and $R^h$ are each independently a hydrogen atom, a $C_{1-6}$ alkyl group, a formyl group, a $C_{1-6}$ alkylcarbonyl group, a $C_{1-6}$ haloalkylcarbonyl group, a $C_{3-8}$ cycloalkylcarbonyl group, a $C_{1-6}$ alkoxycarbonyl group, a substituted or unsubstituted amidino group, a substituted or unsubstituted aminocarbonyl group, a substituted or unsubstituted aminosulfonyl group, or a $C_{1-6}$ haloalkylsulfonyl group.

2. A pest control agent comprising at least one selected from the group consisting of the compound according to claim 1 and a salt thereof as an active ingredient.

3. An insecticidal or acaricidal agent comprising at least one selected from the group consisting of the compound according to claim 1 and a salt thereof as an active ingredient.

4. An ectoparasite control agent comprising at least one selected from the group consisting of the compound according to claim 1 and a salt thereof as an active ingredient.

5. An endoparasite control agent or endoparasite-expelling agent comprising at least one selected from the group consisting of the compound according to claim 1 and a salt thereof as an active ingredient.

* * * * *